(12) United States Patent
Killian et al.

(10) Patent No.: US 10,745,731 B2
(45) Date of Patent: Aug. 18, 2020

(54) RECOMBINANT PRODUCTION METHOD

(71) Applicant: Hoffmann-La Roche Inc., Little Falls, NJ (US)

(72) Inventors: Tobias Killian, Penzberg (DE); Markus Neubauer, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 80 days.

(21) Appl. No.: 16/004,992

(22) Filed: Jun. 11, 2018

(65) Prior Publication Data

US 2019/0002947 A1   Jan. 3, 2019

Related U.S. Application Data

(63) Continuation of application No. PCT/EP2016/081120, filed on Dec. 15, 2016.

(30) Foreign Application Priority Data

Dec. 16, 2015  (EP) .................................... 15200528

(51) Int. Cl.
| | |
|---|---|
| *C12P 5/00* | (2006.01) |
| *C12P 21/02* | (2006.01) |
| *C12N 5/00* | (2006.01) |
| *C12N 5/071* | (2010.01) |
| *C07K 16/44* | (2006.01) |

(52) U.S. Cl.
CPC ............ *C12P 21/02* (2013.01); *C12N 5/0018* (2013.01); *C12N 5/0602* (2013.01); *C07K 16/44* (2013.01); *C12N 2500/30* (2013.01); *C12N 2501/11* (2013.01); *C12N 2501/2301* (2013.01); *C12N 2501/25* (2013.01); *C12N 2510/00* (2013.01)

(58) Field of Classification Search
None
See application file for complete search history.

(56) References Cited

U.S. PATENT DOCUMENTS

2009/0023186 A1   1/2009   Hildinger et al.

FOREIGN PATENT DOCUMENTS

| WO | 2010/050903 A1 | 5/2010 |
|---|---|---|
| WO | 2014/022758 A1 | 2/2014 |
| WO | 2015/000624 A1 | 1/2015 |
| WO | 2015/036583 A2 | 3/2015 |
| WO | 2015/036583 A3 | 3/2015 |

OTHER PUBLICATIONS

Arts et al., Clinical Cancer Research 15(22):6841-6851 ( 2009).
Ashburner et al., "The p65 (RelA) subunit of NF-kappaB interacts with the histone deacetylase (HDAC) corepressors HDAC1 and HDAC2 to negatively regulate gene expression" Molecular and Cellular Biology 21(20):7065-7077 ( 2001).
Atadja et al., "Development of the pan-DAC inhibitor panobinostat (LBH589): successes and challenges" Cancer Letters 280:233-241 ( 2009).
Backliwal et al., "Valproic acid: A viable alternative to sodium butyrate for enhancing protein expression in mammalian cell cultures" Biotechnology and Bioengineering 101(1):182-189 ( 2008).
Baeuerle et al., "I kappa B: a specific inhibitor of the NF-kappa B transcription factor." Science 242:540-546 ( 1988).
Balasubramanian et al., "A novel histone deacetylase 8 (HDAC8)-specific inhibitor PCI-34051 induces apoptosis in T-cell lymphomas" Leukemia 22:1026-1034 ( 2008).
Baldwin et al., "The NF-κB and IκB Proteins: New Discoveries and Insights" Ann Rev Immunol 14:649-683 ( 1996).
Bantscheff et al., "Chemoproteomics profiling of HDAC inhibitors reveals selective targeting of HDAC complexes" Nature Biotechnology 29(3):255-265 ( 2011).
Bertrand et al., "Inside HDAC with HDAC inhibitors" Eur J Mec Chem 45:2095-2116 ( 2010).
Biswas et al., "Epidermal growth factor-induced nuclear factor kappa B activation: A major pathway of cell-cycle progression in estrogen-receptor negative breast cancer cells" Proceedings of the National Academy of Sciences 97(15):8542-8547 ( 2000).
Bjerkedal et al., "Valproic acid and spina bifida" Lancet (London, England) 2:1096 ( 1982).
Blaheta et al., "Anti-tumor mechanisms of valproate: a novel role for an old drug" Medicinal Research Reviews 22(5):492-511 ( 2002).
Blaheta et al., "Evolving anticancer drug valproic acid: insights into the mechanism and clinical studies" Medicinal Research Reviews 25(4):383-397 ( 2005).
Bode et al., "Post-translational modification of p53 in tumorigenesis" Nature reviews. Cancer 4:793-805 ( 2004).
Bolden et al., "Anticancer activities of histone deacetylase inhibitors" Nature Reviews. Drug discovery 5:769-784 ( 2006).
Bolton et al., "PubChem: Integrated Platform of Small Molecules and Biological Activities" Annual Reports in Computational Chemistry 4:217-241 ( 2008).
Burli et al., "Design, synthesis, and biological evaluation of potent and selective class IIa histone deacetylase (HDAC) inhibitors as a potential therapy for Huntington's disease" Journal of Medicinal Chemistry 56:9934-9954 ( 2013).
Caillaud et al., "Acetylation of Interferon Regulatory Factor-7 by p300/CREB-binding Protein (CBP)-associated Factor (PCAF) Impairs its DNA Binding" Journal of Biological Chemistry 277(51):49417-49421 ( 2002).

(Continued)

*Primary Examiner* — Mindy G Brown
(74) *Attorney, Agent, or Firm* — Daphne Reddy

(57) ABSTRACT

Herein is reported a method for the recombinant production of a polypeptide in a eukaryotic cell comprising the steps of (i) cultivating a eukaryotic cell comprising a nucleic acid encoding the polypeptide in a cultivation medium comprising a compound selected from the group consisting of trans-2-methyl 2-pentenoic acid, the broad-spectrum HDAC inhibitor Quisinostat, and the subtype-specific HDAC inhibitor Romidepsin, and (ii) recovering the polypeptide from the cell or the cultivation medium and thereby producing the polypeptide in a eukaryotic cell.

22 Claims, 7 Drawing Sheets

(56) References Cited

OTHER PUBLICATIONS

Chateauvieux et al., "Molecular and Therapeutic Potential and Toxicity of Valproic Acid" Journal of Biomedicine and Biotechnology 2010:1-18 ( 2010).
Chen et al., "Acetylation of RelA at discrete sites regulates distinct nuclear functions of NF-kappaB" The EMBO Journal 21(23):6539-6548 ( 2002).
Chen et al., "Chronic Sodium Valproate Selectively Decreases Protein Kinase C a and e In Vitro" Journal of Neurochemistry 63:2361-2364 ( 1994).
Chen et al., "Construction, expression, purification and functional analysis of recombinant NFkappaB p50/p65 heterodimer" Protein engineering 12(5):423-428 ( 1999).
Chen et al., "Duration of nuclear NF-kappaB action regulated by reversible acetylation." Science 293:1653-1657 ( 2001).
Chen et al., "Lithium regulates PKC-mediated intracellular crosstalk and gene expression in CNS in vivo" Bipolar Disorders 2:217-236 ( 2000).
Chen et al., "Site-specific phosphorylation of IkappaBalpha by a novel ubiquitination-dependent protein kinase activity." Cell 84:853-862 ( 1996).
Chen et al., "The Mood-Stabilizing Agent Valproate Inhibits the Activity of Glycogen Synthase Kinase-3" J. Neurochem 72(3):1327-1330 ( 1999).
Chou et al., "Pimelic diphenylamide 106 is a slow, tight-binding inhibitor of class I histone deacetylases." The Journal of biological chemistry 283(51):35402-35409 ( 2008).
Chung et al., "Characterization of the histone core complex" Proc. Natl. Acad. Sci. USA 75(4):1680-1684 ( 1978).
Clapier et al., "The biology of chromatin remodeling complexes" Annual Review of Biochemistry 78:273-304 ( 2009).
Dai et al., "Blockade of Histone Deacetylase Inhibitor-Induced RelA/p65 Acetylation and NF-B Activation Potentiates Apoptosis in Leukemia Cells through a Process Mediated by Oxidative Damage, XIAP Downregulation, and c-Jun N-Terminal Kinase 1 Activation" Molecular and Cellular Biology 25(13):5429-5444 ( 2005).
DiDonato et al., "A cytokine-responsive IkappaB kinase that activates the transcription factor NF-kappaB." Nature 388:548-554 ( 1997).
Eickholt et al., "Effects of Valproic Acid Derivatives on Inositol Trisphosphate Depletion, Teratogenicity, Glycogen Synthase Kinase-3 Inhibition, and Viral Replication: A Screening Approach for New Bipolar Disorder Drugs Derived from the Valproic Acid Core Structure" Molecular Pharmacology 67(5):1426-1433 ( 2005).
Eikel et al., "Teratogenic Effects Mediated by Inhibition of Histone Deacetylases: Evidence from Quantitative Structure Activity Relationships of 20 Valproic Acid Derivatives" Chem. Res. Toxicol. 19:272-278 ( 2006).
Eyal et al., "Histone deacetylases inhibition and tumor cells cytotoxicity by CNS-active VPA constitutional isomers and derivatives." Biochemical Pharmacology 69:1501-1508 ( 2005).
Fischle et al., "In nucleo enzymatic assays for the identification and characterization of histone modifying activities" Methods 36:362-367 ( 2005).
Fontes et al., "The projection score—an evaluation criterion for variable subset selection in PCA visualization" BMC Bioinformatics 12(307):1-17 ( 2011).
Fujik et al., "A proapoptotic effect of valproic acid on progenitors of embryonic stem cell-derived glutamatergic neurons" Cell Death & Disease 4:e677-e677 ( 2013).
Furumai et al., "FK228 (Depsipeptide) as a Natural Prodrug That Inhibits Class I Histone Deacetylases1" Cancer Research 62:4916-4921 ( 2002).
Giavini et al., "Teratogenic activity of HDAC inhibitors" Current Pharmaceutical Design 20:5438-5442 ( 2014).
Gloire et al., "NF-kappaB activation by reactive oxygen species: fifteen years later" Biochemical pharmacology 72:1493-1505 ( 2006).
Göttlicher et al., "Valproic acid defines a novel class of HDAC inhibitors inducing differentiation of transformed cells" The EMBO Journal 20(24):6969-6978 ( 2001).
Grimm et al., "The inducible transcription factor NF-κB: structure-function relationship of its protein subunits" Biochemical Journal 290:297-308 ( 1993).
Gurvich et al., "Histone deacetylase is a target of valproic acid-mediated cellular differentiation" Cancer Research 64:1079-1086 ( 2004).
Hacker et al., "Polyethyleneimine-based transient gene expression processes for suspension-adapted HEK-293E and CHO-DG44 cells" Protein Expression and Purification 92:67-76 ( 2013).
Han et al., "Valproic acid inhibits the growth of HeLa cervical cancer cells via caspase-dependent apoptosis" Oncology Reports 30:2999-3005 ( 2013).
Hayashi et al., "The innate immune response to bacterial flagellin is mediated by Toll-like receptor 5" Nature 410(6832):1099-1103 ( 2001).
Hebbar et al., "Altered Histone H1 Stoichiometry and an Absence of Nucleosome Positioning on Transfected DNA" Journal of Biological Chemistry 283(8):4595-4601 ( 2008).
Heusch et al., "The generation of nfkb2 p52: mechanism and efficiency" Oncogene 18:6201-6208 ( 1999).
Holden et al., "Phorbol ester-stimulated NF-κB-dependent transcription: Roles for isoforms of novel protein kinase C" Cellular Signalling 20:1338-1348 ( 2008).
ISR of PCT/EP2016/081120 (Date of mailing Feb. 15, 2017).
Jenuwein et al., "Translating the histone code" Science 293:1074-1080 ( 2001).
Jiang et al., "Nucleosome positioning and gene regulation: advances through genomics." Nature reviews. Genetics 10:161-172 ( 2009).
Kasperczyk et al., "Betulinic acid as new activator of NF-kappaB: molecular mechanisms and implications for cancer therapy." Oncogene 24:6945-6956 ( 2005).
Khan et al., "Determination of the class and isoform selectivity of small-molecule histone deacetylase inhibitors" The Biochemical Journal 409:581-589 ( 2008).
Khobta et al., "Gene silencing induced by oxidative DNA base damage: association with local decrease of histone H4 acetylation in the promoter region" Nucleic acids research 38(13):4285-4295 ( 2010).
Kramer et al., "Causal analysis approaches in Ingenuity Pathway Analysis" Bioinformatics 30(4):523-530 ( 2014).
Kuriyan et al., "Structure of the NF-κB transcription factor: a holistic interaction with DNA" Structure 3:135-141 ( 1995).
Lallena et al., "Activation of IkappaB kinase beta by protein kinase C isoforms." Molecular and Cellular Biology 19(3):2180-2188 ( 1999).
Leszczyniecka et al., "Differentiation therapy of human cancer: basic science and clinical applications" Pharmacology & Therapeutics 90:105-156 ( 2001).
Li et al., "The role of chromatin during transcription" Cell 128:707-719 ( 2007).
Lin et al., "A glycine-rich region in NF-kappaB p105 functions as a processing signal for the generation of the p50 subunit." Molecular and Cellular Biology 16(5):2248-2254 ( 1996).
Ludtmann, et al., "Molecular pharmacology in a simple model system: Implicating MAP kinase and phosphoinositide signalling in bipolar disorder" Seminars in Cell & Developmental Biology 22:105-112 ( 2011).
Luger et al., "Crystal structure of the nucleosome core particle at 2.8 A resolution." Nature 389:251-260 ( 1997).
Malvaez et al., "HDAC3-selective inhibitor enhances extinction of cocaine-seeking behavior in a persistent manner." Proceedings of the National Academy of Sciences 110(7):2647-2652 ( 2013).
Martin et al., "The anticonvulsant valproate teratogen restricts the glial cell cycle at a defined point in the mid-G1 phase" Brain Research 554:223-228 ( 1991).
May et al., "Rel/NF-kappa B and I kappa B proteins: an overview." Seminars in Cancer Biology 8:63-73 ( 1997).
Minucci et al., "Histone deacetylase inhibitors and the promise of epigenetic (and more) treatments for cancer." Nature reviews. Cancer 6:38-51 ( 2006).

(56) References Cited

OTHER PUBLICATIONS

Osborn et al., "Tumor necrosis factor alpha and interleukin 1 stimulate the human immunodeficiency virus enhancer by activation of the nuclear factor kappa B" Proc. Natl. Acad. Sci. USA 86:2336-2340 (1989).

Phiel et al., "Histone deacetylase is a direct target of valproic acid, a potent anticonvulsant, mood stabilizer, and teratogen" The Journal of Biological Chemistry 276(39):36734-36741 (2001).

Pierce et al., "Novel inhibitors of cytokine-induced IkappaBalpha phosphorylation and endothelial cell adhesion molecule expression show anti-inflammatory effects in vivo" The Journal of Biological Chemistry 272(34):21096-21103 (1997).

Riu et al., "Histone Modifications are Associated with the Persistence or Silencing of Vector-mediated Transgene Expression In Vivo" Molecular Therapy 15(7): 1348-1355 (2007).

Ropero et al., "The role of histone deacetylases (HDACs) in human cancer" Molecular Oncology 1:19-25 (2007).

Sen et al., "Epidermal growth factor activation of NF-kappaB is mediated through IkappaBalpha degradation and intracellular free calcium." Cell 47:921-928 (1986).

Slesinger et al., "Effects of Anticonvulsants on Cell Growth and Enzymatic and Receptor Binding Activity in a Neuroblastoma X Glioma Hybrid Cell Culture" Epilepsia 28(3):214-221 (1987).

Struhl et al., "Fundamentally different logic of gene regulation in eukaryotes and prokaryotes" Cell 98:1-4 (1999).

Sun et al., "Epidermal growth factor activation of NF-kappaB is mediated through IkappaBalpha degradation and intracellular free calcium" Oncogene 16:2095-2102 (1998).

Suzuki et al., "Plasmid DNA sequences present in conventional herpes simplex virus amplicon vectors cause rapid transgene silencing by forming inactive chromatin" Journal of Virology 80(7):3293-3300 (2006).

Totzke et al., "A novel member of the IkappaB family, human IkappaB-zeta, inhibits transactivation of p65 and its DNA binding" The Journal of Biological Chemistry 281:12645-12654 (2006).

Verstrepena et al., "TLR-4, IL-1R and TNF-R signaling to NF-kappaB: variations on a common theme" Cell. Mol. Life Sci. 65:2964-2978 (2008).

Werling et al., "Induction of Differentiation in F9 Cells and Activation of Peroxisome Proliferator-Activated Receptor d by Valproic Acid and Its Teratogenic Derivatives" Molecular Pharmacology 59(5):1269-1276 (2001).

Woodcock et al., "Structural repeating units in chromatin. I. Evidence for their general occurrence." Experimental Cell Research 97:101-110 (1976).

Xu et al., "Histone deacetylase inhibitors: molecular mechanisms of action" Oncogene 26:5541-5552 (2007).

Yamaoka et al., "Complementation cloning of NEMO, a component of the IkappaB kinase complex essential for NF-kappaB activation." Cell 93:1231-1240 (1998).

Yuan et al., "Stat3 dimerization regulated by reversible acetylation of a single lysine residue" Science 307:269-273 (2005).

Yuan et al., "The Mood Stabilizer Valproic Acid Activates Mitogen-activated Protein Kinases and Promotes Neurite Growth" The Journal of Biological Chemistry 276(34):31674-31683 (2001).

Zilberman et al., "Regulation of microtubule dynamics by inhibition of the tubulin deacetylase HDAC6" Journal of Cell Science 122:3531-3541 (2009).

RECOMBINANT PRODUCTION METHOD

CROSS REFERENCE TO RELATED APPLICATIONS

This application is a continuation of International Application No. PCT/EP2016/081120 having an International Filing Date of 15 Dec. 2016, the entire contents of which are incorporated herein by reference, and which claims the benefit of priority under 35 U.S.C. § 119 to EP 15200528.6 filed 16 Dec. 2015.

FIELD OF THE INVENTION

The current invention is in the field of the recombinant production of heterologous polypeptides in eukaryotic cells. In more detail herein is reported a method for the production of a polypeptide wherein a production enhancer is added to the cultivation medium.

BACKGROUND

Therapeutic antibodies have become an important therapeutic modality in drug development. New technologies in antibody engineering enable manifold possibilities in antibody design like alterations in valency, specificity and affinity resulting in a great spectrum of different antibodies. In order to identify and select antibodies, a large number of potential therapeutics has to be evaluated to identify promising candidates during early drug development. For this reason, there is a great interest in fast and efficient production of those recombinant proteins for research and early drug development.

Antibodies are complex biomolecules, requiring post-translational modifications like glycosylation and correct folding to gain full bioactivity, and therefore, mammalian cells are the major employed cells for recombinant production. There are two methods to produce antibodies in these cells: stable and transient gene expression. Stable gene expression is a very effective way to produce recombinant antibodies because the encoding nucleic acids integrate into the genome of the host cell, what enables their continuous expression. However, the generation of a cell line stably expressing the antibody is very labor- and time-consuming. Hence, transient gene expression is the method of choice in early drug development, as it offers the solution for the need of rapidly producing the material necessary. Albeit gene expression is not continuous with this method, it is possible to produce the recombinant antibody within a few days.

Valproic Acid (VPA) is a short chain fatty acid used in the clinic as an anticonvulsive agent and mood-stabilizing drug (Blaheta et al.; 2005). It is mostly applied to treat epilepsy, bipolar disorders or migraine headache. Since VPA inhibits proliferation, induces apoptosis and induces differentiation of a variety of tumor cells, it is often implicated in the treatment of cancer. Recent studies identified several additional cellular pathways affected by VPA, like PKC inhibition, Wnt-signaling activation and ERK activation (Fujiki et al.; 2013). Another interesting feature of VPA is its ability to inhibit histone deacetylases (HDACs) (Gottlicher et al.; 2001).

Valproic acid (VPA) is commonly used for transient gene expression (TGE) enhancement. As histone inhibitory activity was discovered for VPA it was proposed that its effect on TGE is mediated by inhibiting the deacetylation of histone tails. This hypothesis arose because it is assumed that transiently transfected plasmids integrate into the chromatin structure and therefore underlie epigenetic regulation of gene expression by histone modification.

However, VPA treatment also decreases viable cell density (VCD) and cell viability of the cells. Therefore, VPA was shown to induce not only cell cycle arrest but subsequently also the extrinsic as well as the intrinsic apoptotic pathway, respectively (Xu et al.; 2007). Thus, combined treatment of VPA with caspase inhibitors significantly prevented apoptotic cell death induced by VPA (Han et al.; 2013).

Backliwal, G., et al. (Biotechnol. Bioeng. (2008)) reported that valproic acid is a viable alternative to sodium butyrate for enhancing protein expression in mammalian cell culture. It is suggested herein that the effect of valproic acid is based on a histone deacetylase inhibition (HDACi).

It was shown in various cell lines including human embryonic kidney (HEK) 293 cells that VPA directly inhibits histone deacetylases (HDACs) (Gottlicher, Minucci et al. 2001). Confirming this observation, hyperacetylation of Histone H4 was observed after VPA treatment (Phiel, Zhang et al. 2001).

In US 2009/023186 the use of valproic acid for enhancing production of recombinant proteins in mammalian cells is reported.

In WO 2015/000624 a method for producing antibodies using ovine b-cells and uses thereof is reported.

In WO 2010/050903 chimeric Flagellins for vaccines are reported.

In WO 2015/036583 the combination of epigenetic factors and bispecific compounds targeting CD33 and CD3 in the treatment of myeloid leukemia is reported.

In WO 2014/022758 a single agent anti-PD-L1 and PD-L2 dual binding antibodies and methods of use is reported.

R. Furumai reported FK228 (Depsipeptide) as a natural prodrug that inhibits class I histone deacetylases (Cancer Res. 62 (2002) 4916).

SUMMARY OF THE INVENTION

Herein are reported methods for increasing the transient gene expression yield using production enhancers that have reduced cytotoxicity e.g. compared to the known production enhancer valproic acid.

One aspect as reported herein is a method for the recombinant production of a polypeptide in a eukaryotic cell comprising the steps of:
  cultivating a eukaryotic cell comprising a nucleic acid encoding the polypeptide in a cultivation medium comprising a (canonical) NFκB activator, and
  recovering the polypeptide from the cell or the cultivation medium and thereby producing the polypeptide in a eukaryotic cell.

In one embodiment the (canonical) NFκB activator is selected from the group consisting of TNFalpha, ligands of members of the interleukin-1/Toll-like receptor (IL-1R/TLR) family, e.g. Flagellin, lipopolysaccharide and interleukin-1beta.

One aspect as reported herein is a method for the recombinant production of a polypeptide in a eukaryotic cell comprising the steps of:
  cultivating a eukaryotic cell comprising a nucleic acid encoding the polypeptide in a cultivation medium comprising 2M2P or Quisinostat or Romidepsin, and
  recovering the polypeptide from the cell or the cultivation medium and thereby producing the polypeptide in a eukaryotic cell.

In one embodiment 2M2P or Quisinostat or Romidepsin is added of from one hour to 24 hours after the after transfection of the cells to the cultivation. In one embodiment 2M2P or Quisinostat or Romidepsin is added about three hours after the transfection of the cells to the cultivation. Thus, in one embodiment the cultivating is in a cultivation medium to which 2M2P or Quisinostat or Romidepsin has been added after the transfection.

In one embodiment 2M2P (trans-2-methyl 2-pentenoic acid) is added to a final concentration in the cultivation medium of about 6-7 mM (at least 3 mM).

One aspect as reported herein is a method for the recombinant production of a polypeptide in a eukaryotic cell comprising the steps of:
cultivating a eukaryotic cell comprising a nucleic acid encoding the polypeptide in a cultivation medium comprising an atypical/non-canonical NFκB activator, and
recovering the polypeptide from the cell or the cultivation medium and thereby producing the polypeptide in a eukaryotic cell.

In one embodiment the non-canonical NFκB activator is selected from the group consisting of EGF, PMA, and betulinic acid.

One aspect as reported herein is a method for the recombinant production of a polypeptide in a eukaryotic cell comprising the steps of:
cultivating a eukaryotic cell comprising a nucleic acid encoding the polypeptide in a cultivation medium comprising a subtype-specific HDAC inhibitor, and
recovering the polypeptide from the cell or the cultivation medium and thereby producing the polypeptide in a eukaryotic cell.

In one embodiment the subtype-specific HDAC inhibitor is an HDAC-1 and/or HDAC-2 and/or HDAC-3 inhibitor. In one embodiment the subtype-specific HDAC inhibitor is selected from the group consisting of pimelic diphenylamide 106, Apicidin, and Romidepsin.

In the above methods different functional pathways are modified in order to increase transient gene expression yield. It has now been found that a further increase in transient gene expression yield is possible if production enhancers using different modes of action, i.e. modifying different functional pathways, are combined. The combination of production enhancer modifying the same functional pathway did not result in a significant further increase in transient gene expression yield.

One aspect as reported herein is a method for the recombinant production of a polypeptide in a eukaryotic cell comprising the steps of:
cultivating a eukaryotic cell comprising a nucleic acid encoding the polypeptide in a cultivation medium comprising two members of the group consisting of canonical and non-canonical NFκB activators, trans-2-methyl 2-pentenoic acid and subtype-specific HDAC inhibitors, and
recovering the polypeptide from the cell or the cultivation medium and thereby producing the polypeptide in a eukaryotic cell.

One aspect as reported herein is a method for the recombinant production of a polypeptide in a eukaryotic cell comprising the steps of:
cultivating a eukaryotic cell comprising a nucleic acid encoding the polypeptide in a cultivation medium comprising a compound selected from the group consisting of trans-2-methyl 2-pentenoic acid and HDAC inhibitors chemically distinct from short chain fatty acids derivatives and
recovering the polypeptide from the cell or the cultivation medium and thereby producing the polypeptide in a eukaryotic cell.

One aspect as reported herein is a method for the recombinant production of a polypeptide in a eukaryotic cell comprising the steps of:
cultivating a eukaryotic cell comprising a nucleic acid encoding the polypeptide in a cultivation medium comprising Flagellin and trans-2-methyl 2-pentenoic acid, and
recovering the polypeptide from the cell or the cultivation medium and thereby producing the polypeptide in a eukaryotic cell.

One aspect as reported herein is a method for the recombinant production of a polypeptide in a eukaryotic cell comprising the steps of:
cultivating a eukaryotic cell comprising a nucleic acid encoding the polypeptide in a cultivation medium comprising Quisinostat and trans-2-methyl 2-pentenoic acid, and
recovering the polypeptide from the cell or the cultivation medium and thereby producing the polypeptide in a eukaryotic cell.

One aspect as reported herein is a method for the recombinant production of a polypeptide in a eukaryotic cell comprising the steps of:
cultivating a eukaryotic cell comprising a nucleic acid encoding the polypeptide in a cultivation medium comprising Romidepsin and one of trans-2-methyl 2-pentenoic acid and Flagellin, and
recovering the polypeptide from the cell or the cultivation medium and thereby producing the polypeptide in a eukaryotic cell.

In one embodiment 2M2P is added to a final concentration in the cultivation medium of about 6-7 mM (about 3 hours after transfection).

In one embodiment Flagellin or Romidepsin are added at a concentration of 2 ng/mL and 15 nM, respectively, 27 h after transfection.

In one embodiment the eukaryotic cell is a mammalian cell. In one embodiment the mammalian cell is a CHO cell or a HEK cell. In one preferred embodiment the mammalian cell is a HEK293 cell.

In one embodiment the expression is a stable or a transient expression. In one preferred embodiment the expression is a transient expression.

In one embodiment the cultivation is for 3 to 16 days. In one embodiment the cultivation is for 3-10 days, preferably if the cell is a HEK cell. In one preferred embodiment the cultivation is for about 7 days.

DESCRIPTION OF THE FIGURES

FIG. 2A: determination of the most effective concentration; JNJ=Quisinostat; PXD=Belinostat; SAHA=suberoylanilide hydroxamic acid (Vorinostat);

FIG. 2B: N=2 for each treatment (except 5: N=1); y-axis: relative cell specific productivity [%]; 1: control, 2: valproic acid, 3: pimelic diphenylamide 106, 4: TMP269, 5: Bufexamac, 6: Belinostat, 7: Entinostat, 8: Mocetinostat, 9: Quisinostat.

FIG. 3A: HDAC inhibitory activity of different compounds; HEK293F cells were incubated with indicated molecules as well as a substrate converted to a fluorescent dye after deacetylation; HDAC inhibitory activity was calculated based on the strength of fluorescent signal; HEK293F cells incubated without substrate are indicated as negative control; HEK293F cells incubated with substrate and 10 µM of the broad spectrum HDAC inhibitor Trichostatin A is indicated as positive control; N=3 for each treatment; levels of significance: n.s.: p≥0.05; one asterisk: p≤0.05; two asterisks p≤0.01; three asterisks p≤0.001;

Figure 3A:
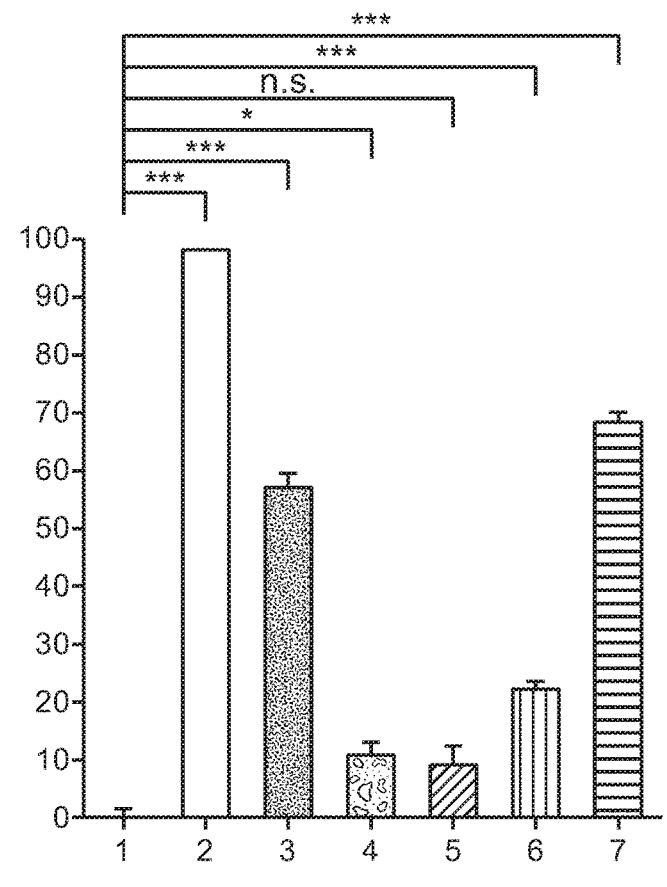
FIGS. 3A and 3B.
Figure 3B:
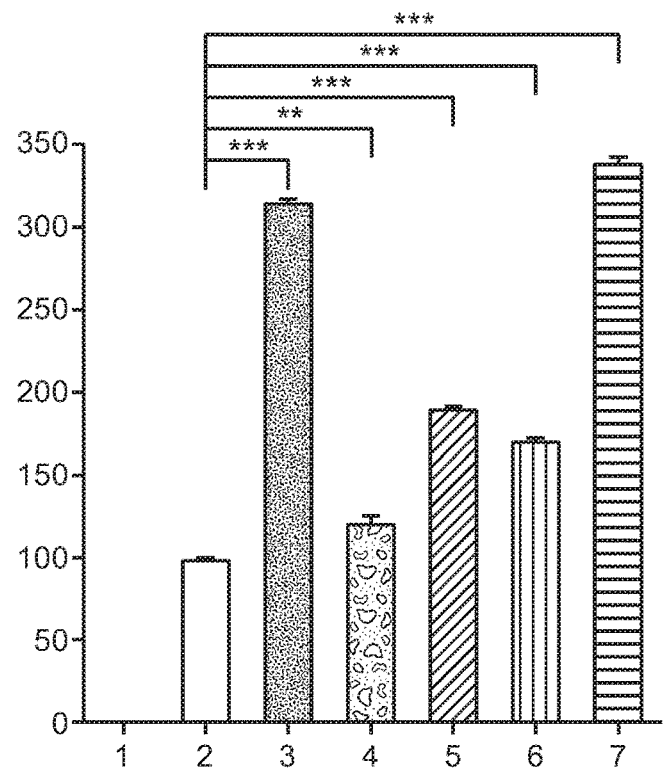

y-axis: relative HDAC inhibition [%]; 1: control, 2: 10 µM TSA (positive control), 3: 3 mM valproic acid, 4: 3 mM valnoctamide, 5: 3 mM 2M2P, 6: 20 µM pimelic diphenylamide 106, 7: 300 nM Quisinostat;

FIG. 3B: Relative cell specific productivity for different treatments using VPA and analogues and HDAC inhibitors; N=3 for each treatment; levels of significance: two asterisks: p≤0.01; three asterisks p≤0.001;

y-axis: relative cell specific productivity [%]; 1: control, not-transfected, 2: control, transfected, 3: 3 mM valproic acid, 4: 3 mM valnoctamide, 5: 3 mM 2M2P, 6: 20 µM pimelic diphenylamide 106, 7: 300 nM Quisinostat.

Figure 4:
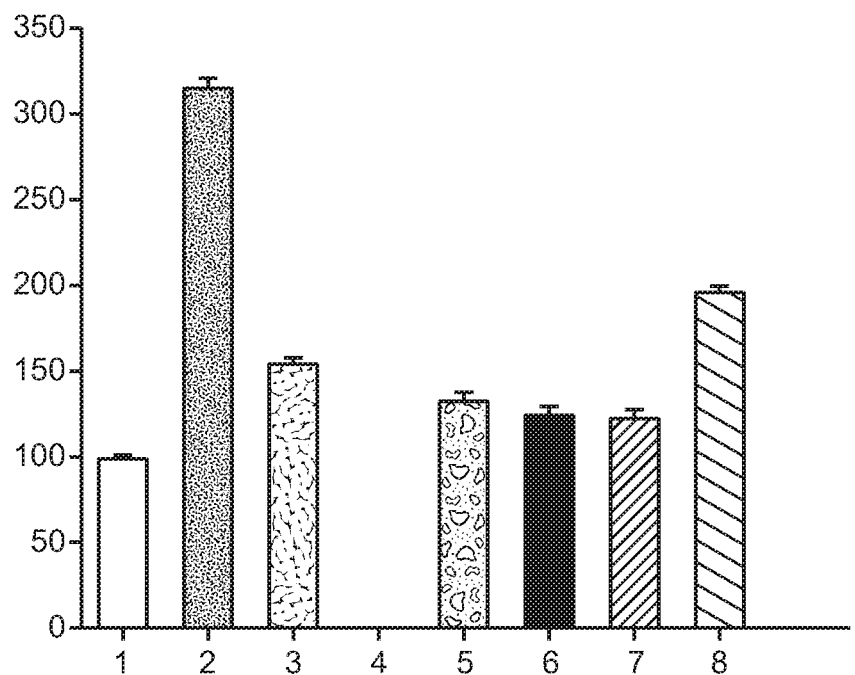

FIG. 4: Effect of VPA analogues on cell specific productivity; N=2 for each treatment; y-axis: relative cell specific productivity [%]; 1: control, 2: valproic acid—4 mM, 3: valpromide—2 mM, 4: valpromide—3 mM, 5: valnoctamide—2 mM, 6: valnoctamide—3 mM, 7: 2M2P—2 mM, 8: 2M2P—3 mM.

Figure 5:
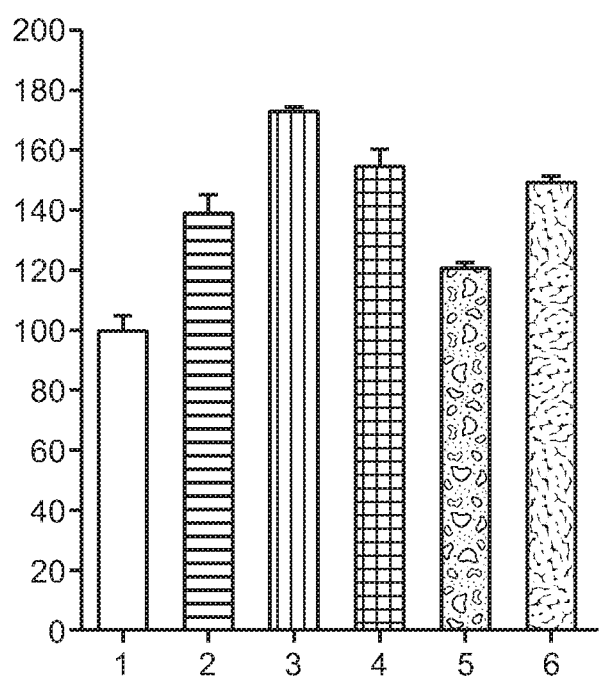

FIG. 5: Effect of various NFκB activators on cell specific productivity; N=2 for each treatment; y-axis: relative cell specific productivity [X]; 1: control (transfected), 2: 50 ng/mL TNFalpha, 3: 50 ng/mL EGF, 4: 10 ng/mL Flagellin, 5: 10 µM betulinic acid, 6: 100 nM phorbol myristate acetate.

Figure 6A:
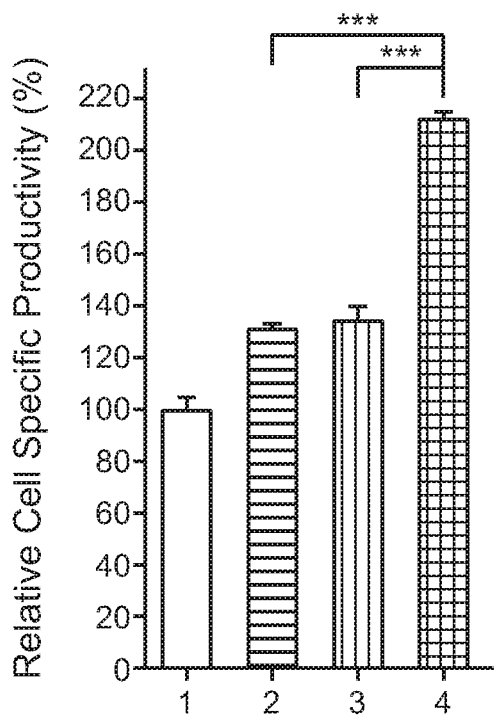
Figure 6B:
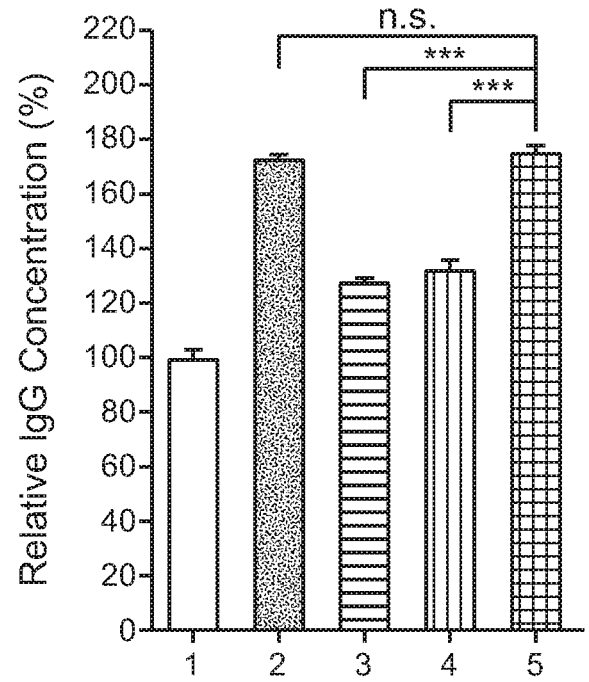

FIGS. 6A and 6B: Effect on cell specific productivity (FIG. 6A) and IgG concentration (FIG. 6B) after treatment with 2M2P and Flagellin; N=3 for each treatment; levels of significance: n.s.: p≥0.05; three asterisks p≤0.001; every treatment showed significant increase compared to the negative control p≤0.001;

FIG. 6A: y-axis: relative cell specific productivity [%]; 1: control (transfected), 2: 3 mM 2M2P, 3: 2 ng/mL Flagellin, 4: 3 mM 2M2P+2 ng/mL Flagellin;

FIG. 6B: y-axis: relative IgG concentration [%]; 1: control (transfected), 2: 4 mM valproic acid, 2: 3 mM 2M2P, 4: 2 ng/mL Flagellin, 5: 3 mM 2M2P+2 ng/mL Flagellin.

Figure 7:
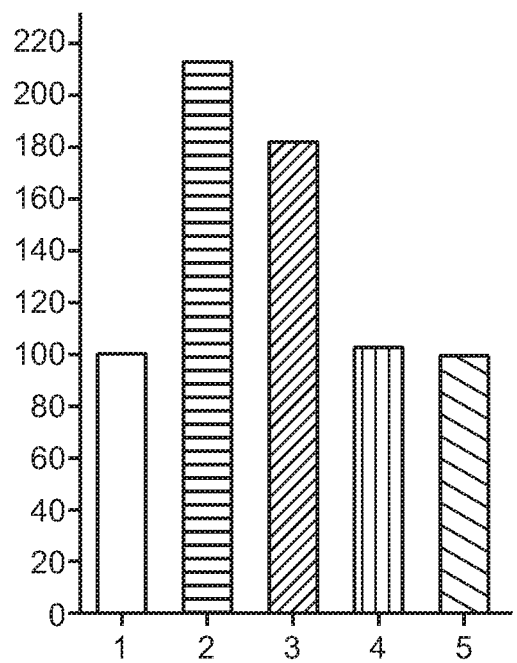

FIG. 7: Differential class I HDAC isoform inhibition; N=1 for each treatment; y-axis: relative IgG concentration [%]; 1: control (transfected), 2: 10 nM Romidepsin, 3: 200 nM apicidin, 4: 1 µM RGFP966, 5: 5 µM PCI34051.

Figure 8A:
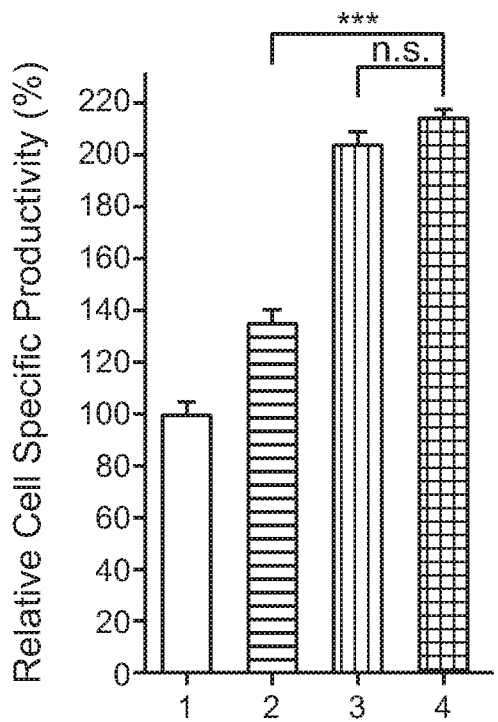
Figure 8B:
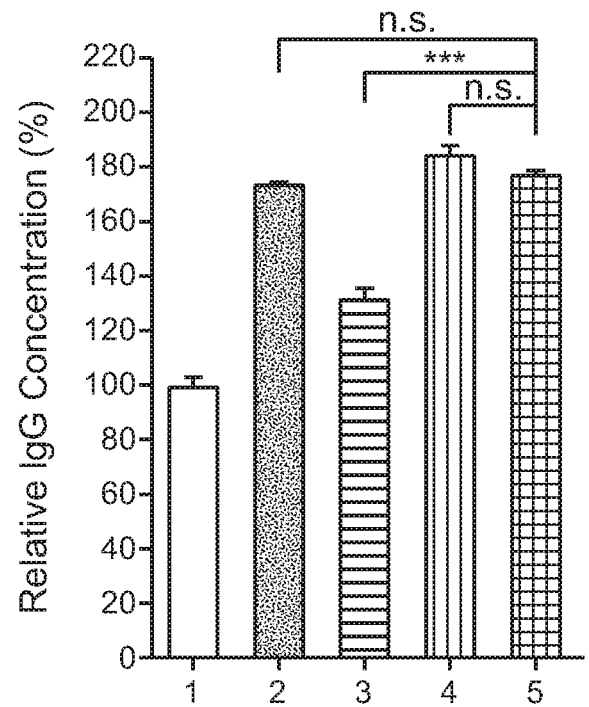

FIGS. 8A and 8B: Effect of NFκB activation and HDAC 1 and 2 inhibition TGE rates; N=3 for each treatment; levels of significance: n.s.: p≥0.05; three asterisks p≤0.001; every treatment showed significant increase compared to the negative control p≤0.01;

FIG. 8A: y-axis: relative cell specific productivity [%]; 1: control (transfected), 2: 2 ng/mL Flagellin, 3: 15 µM Romidepsin, 4: 2 ng/mL Flagellin+15 nM Romidepsin;

FIG. 8B: y-axis: relative IgG concentration [%]; 1: control (transfected), 2: 4 mM valproic acid, 3: 2 ng/mL Flagellin, 4: 15 µM Romidepsin, 5: 2 ng/mL Flagellin+15 nM Romidepsin.

Figure 9A:
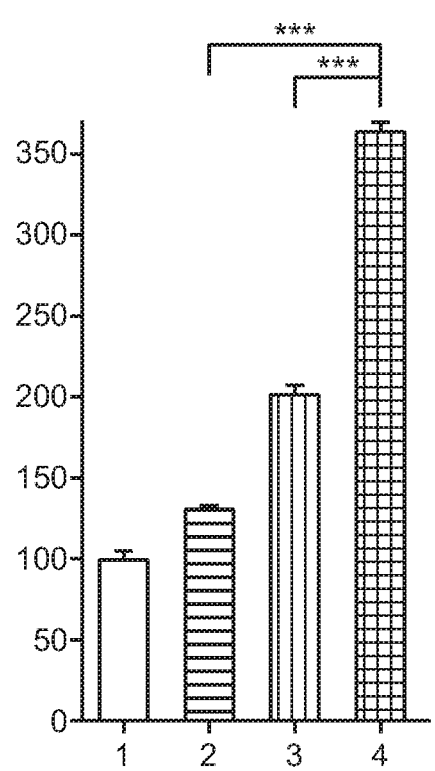
Figure 9B:
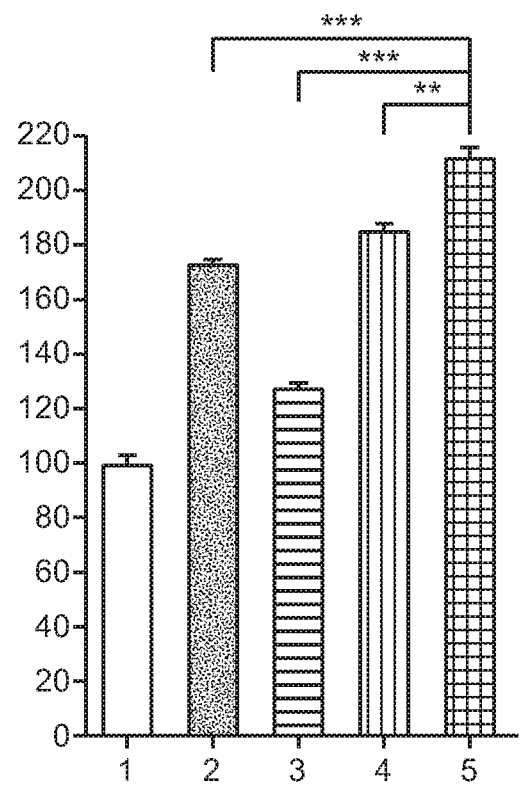

FIGS. 9A and 9B: Effect of the combination of VPA derivative with HDAC 1 and 2 inhibition; N=3 for each treatment; levels of significance: n.s.: p≥0.05; three asterisks p≤0.001; every treatment showed significant increase compared to the negative control p≤0.01;

FIG. 9A: y-axis: relative cell specific productivity; 1: control (transfected), 2: 3 mM 2M2P, 3: 15 nM Romidepsin, 4: 3 mM 2M2P+15 nM Romidepsin;

FIG. 9B: y-axis: relative IgG concentration [%]; 1: control (transfected), 2: 4 mM valproic acid, 3: 3 mM 2M2P, 4: 15 nM Romidepsin, 5: 3 mM 2M2P+15 nM Romidepsin.

DESCRIPTION OF THE ABBREVIATIONS

2M2P: trans-2-methyl 2-pentenoic acid
EGF: epidermal growth factor
ERK: extracellular signal-regulated kinase
FITC: fluorescein isothiocyanate
GAPDH: glyceraldehyde 3-phosphate dehydrogenase
HDAC: histone deacetylase
IκB: inhibitor of NFκB
IKK: IκB kinase
NEMO: NFκB essential modifier
NFκB: nuclear factor kappa-light-chain-enhancer of activated B cells
PD: pimelic diphenylamide 106
PEI: polyethylene imine
TGE: transient gene expression
TNF: tumor necrosis factor
VCM: valnoctamide
VPA: valproic acid, 2-propyl valeric acid, 2-propylpentanoic acid
VPM: valpromide

DETAILED DESCRIPTION OF THE INVENTION

The current invention is based in least in part on the finding that NFκB is a regulator for transient gene expression (TGE) enhancement. This role of NFκB was confirmed by activating NFκB and observing TGE enhancement as well as by inhibiting NFκB after VPA treatment and demonstrating that TGE enhancement could be reduced.

The invention is further based at least in part on the finding that as TGE enhancement mediated by the HDAC inhibitor Quisinostat could also be weakened by NFκB inhibition. TGE enhancement by HDAC inhibition is mediated by NFκB.

The invention is further based at least in part on the finding that as specific inhibition of HDAC 1 and HDAC 2 isoforms by Romidepsin led to a strong increase of TGE yields. These HDAC isoforms are responsible for HDAC-mediated TGE enhancement.

The invention is further based at least in part on the finding that the combination of HDAC inhibition with NFκB activation did not show an additive effect on TGE which further indicates that the same mechanism is affected.

The invention is further based at least in part on the finding that the chemical VPA analogue 2M2P lacking HDAC inhibitory activity at specific concentrations increases TGE, too. Further in contrast to VPA and the HDAC inhibitor, inhibition of NFκB did not lead to a reduction of TGE enhancement mediated by 2M2P. Combination of 2M2P with NFκB activation or HDAC inhibition resulted in additive effects in both cases.

The invention is further based at least in part on the finding that no combined effect was observed when VPA was combined with 2M2P or an HDAC inhibitor.

It has been found that NFκB is a regulator for transient gene expression (TGE) enhancement. Moreover, it has been found that the enhancement by HDAC inhibition is mediated by NFκB activation. It has been further found that specific inhibition of the HDAC isoforms 1 and 2 is sufficient to obtain a TGE enhancement comparable to enhancements mediated by the broad-spectrum HDAC inhibitors VPA and Quisinostat. Further, Romidepsin has been identified as novel TGE enhancer. Further, 2M2P has been identified as novel TGE enhancer. 2M2P has a mode of action independent from HDAC inhibition and NFκB activation. It has been found that the combination of 2M2P with NFκB activation results in a TGE increase comparable to VPA. It has been found that HDAC inhibition is not the only way to enhance TGE rates. Combinatorial studies of VPA with 2M2P or Quisinostat provided evidence that VPA seems to unify the unknown effect of 2M2P and the HDAC inhibitory effect. Finally, it has been found that the combination of 2M2P with isoform-specific HDAC inhibition by Romidepsin provided an enhancer combination with higher potency than VPA.

Definitions

Valproic acid (VPA) denotes 2-propyl valeric acid (2-propylpentanoic acid) and is a short chain fatty acid.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. In contrast thereto reference to "one cell" does not include a plurality of such cells but is limited to a single (isolated) cell.

It is also to be noted that the terms "comprising", "including", and "having" can be used interchangeably.

Further it is also to be noted that the term "comprising" encompasses the term "consisting of" as limitation.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

The terms "full length antibody", "intact antibody," and "whole antibody" are used herein interchangeably to refer to an antibody having a structure substantially similar to a native antibody structure or having heavy chains that contain an Fc region as defined herein.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The Method as Reported Herein

It has been found that NFκB functions as regulator of transient gene expression. NFκB inhibition diminished valproic acid effect on titer. NFκB activation by various molecules resulted in titer increase. This effect can be counteracted by NFκB inhibition.

Thus, herein is reported a method for the recombinant production of a polypeptide in a eukaryotic cell comprising the steps of:
cultivating a eukaryotic cell comprising a nucleic acid encoding the polypeptide in a cultivation medium comprising a canonical NFκB activator, and
recovering the polypeptide from the cell or the cultivation medium and thereby producing the polypeptide in a eukaryotic cell.

The term "a cultivation medium comprising a compound" denotes that at one time point in the cultivation this compound is/has been added to/is present in the cultivation medium. This time point can be directly after the transfection, at the beginning of the cultivation, or at a defined time point after the inoculation of the cultivation (=start of the cultivation). In one embodiment the time point is after the transfection of the cells. In one embodiment the time point is of from one hour to about 30 hours after the transfection of the cells. In one embodiment the time point is about three hours after the transfection of the cells. Thus, in one embodiment the cultivating is in a cultivation medium to which the NFκB activator has been added after the transfection of the cells.

In one embodiment the (canonical) NFκB activator is selected from the group consisting of TNFalpha, ligands of members of the interleukin-1/Toll-like receptor (IL-1R/TLR) family, e.g. Flagellin, lipopolysaccharide and interleukin-1beta.

It has been found that the addition of trans-2-methyl 2-pentenoic acid (2M2P) to the cultivation medium resulted in a transient gene expression titer increase. It has been found that 2M2P enhances TGE via a mechanism independent from NFκB activation as well as HDAC inhibition. It has been found that the enhancement of TGE by 2M2P cannot be reduced by inhibition of IKK and, thus, that specific productivity was improved by a mechanism independent from NFκB.

It has further been found that the addition of Quisinostat or Romidepsin to the cultivation medium resulted in a transient gene expression titer increase.

Thus, herein is reported a method for the recombinant production of a polypeptide in a eukaryotic cell comprising the steps of:
cultivating a eukaryotic cell comprising a nucleic acid encoding the polypeptide in a cultivation medium comprising 2M2P or Quisinostat or Romidepsin, and
recovering the polypeptide from the cell or the cultivation medium and thereby producing the polypeptide in a eukaryotic cell.

In one embodiment 2M2P or Quisinostat or Romidepsin is added of from one hour to 24 hours after transfection of the cells to the cultivation. In one embodiment 2M2P or Quisinostat or Romidepsin is added about three hours after the transfection of the cells to the cultivation. Thus, in one embodiment the cultivating is in a cultivation medium to which 2M2P or Quisinostat or Romidepsin has been added after the transfection.

In one embodiment 2M2P is added to a final concentration in the cultivation medium of about 6-7 mM.

In one embodiment the non-canonical or atypical NFκB activators are selected from the group consisting of but not limited to growth factors, PKC activators or reactive oxygen species-inducing reagents such as betulinic acid.

Thus, herein is reported a method for the recombinant production of a polypeptide in a eukaryotic cell comprising the steps of:
cultivating a eukaryotic cell comprising a nucleic acid encoding the polypeptide in a cultivation medium comprising an atypical/non-canonical NFκB activator, and
recovering the polypeptide from the cell or the cultivation medium and thereby producing the polypeptide in a eukaryotic cell.

NFκB can be activated by EGF via PI3 kinase activation, by PMA via PKC activation or by reactive oxygen species after perturbation of the mitochondrial membrane by betulinic acid, for example (Lallena, Diaz-Meco et al. 1999; Biswas, Cruz et al. 2000; Gloire, Legrand-Poels et al. 2006).

In one embodiment the atypical/non-canonical NFκB activator is selected from the group consisting of EGF, PMA, and betulinic acid.

It has been found that subtype-specific histone deacetylase inhibitors (HDACi) functions as regulator of transient gene expression. The selective inhibition of HDAC-1, HDAC-2 and/or HDAC-3 led to an increase of transient gene expression.

Thus, herein is reported a method for the recombinant production of a polypeptide in a eukaryotic cell comprising the steps of:
 cultivating a eukaryotic cell comprising a nucleic acid encoding the polypeptide in a cultivation medium comprising a subtype-specific HDAC inhibitor, and
 recovering the polypeptide from the cell or the cultivation medium and thereby producing the polypeptide in a eukaryotic cell.

In one embodiment the subtype-specific HDAC inhibitor is an HDAC-1 and/or HDAC-2 and/or HDAC-3 inhibitor. In one embodiment the subtype-specific HDAC inhibitor is selected from the group consisting of pimelic diphenylamide 106, Apicidin, and Romidepsin.

In the above methods different functional pathways are modified in order to increase transient gene expression yield. It has now been found that a further increase in transient gene expression yield is possible if production enhancers using different modes of action, i.e. modifying different functional pathways, are combined. The combination of production enhancer modifying the same functional pathway did not result in a significant further increase in transient gene expression yield.

Thus, herein is reported a method for the recombinant production of a polypeptide in a eukaryotic cell comprising the steps of:
 cultivating a eukaryotic cell comprising a nucleic acid encoding the polypeptide in a cultivation medium comprising two members of the group consisting of canonical and non-canonical NFκB activators, trans-2-methyl 2-pentenoic acid and subtype-specific HDAC inhibitors, and
 recovering the polypeptide from the cell or the cultivation medium and thereby producing the polypeptide in a eukaryotic cell.

The term "a cultivation medium comprising two members of the group consisting of canonical and non-canonical NFκB activators, trans-2-methyl 2-pentanoic acid and subtype-specific HDAC inhibitors" denotes that at one time point in the cultivation these two compounds are present in/have been added to the cultivation medium. This time point can be the transfection, the beginning of the cultivation, or a defined time point after the inoculation of the cultivation (=start of the cultivation). This also includes that the compounds are added sequentially, i.e. one compound is/has been added at a first time point after the transfection of the cells and the respective other compound is/has been added at a second time point after the transfection of the cells. In one embodiment the time point is of from one hour to thirty hours after the transfection of the cells. In one embodiment the first time point is about one to five hours after the transfection of the cells and the second time point is about twenty-one to thirty hours after the transfection of the cells. In one embodiment the first time point is about three hours after the transfection of the cells and the second time point is about twenty-four to twenty-seven hours after the transfection of the cells. Thus, in one embodiment the cultivating is in a cultivation medium to which the two compounds have been added after the inoculation of the cultivation and at a defined time after the transfection of the cells.

Flagellin is a TLR5 agonist. It has been found that the combination of Flagellin with 2M2P resulted in a production yield increase comparable to that obtained with valproic acid.

Thus, herein is reported a method for the recombinant production of a polypeptide in a eukaryotic cell comprising the steps of:
 cultivating a eukaryotic cell comprising a nucleic acid encoding the polypeptide in a cultivation medium comprising Flagellin and trans-2-methyl 2-pentenoic acid, and
 recovering the polypeptide from the cell or the cultivation medium and thereby producing the polypeptide in a eukaryotic cell.

Thus, herein is reported a method for the recombinant production of a polypeptide in a eukaryotic cell comprising the steps of:
 cultivating a eukaryotic cell comprising a nucleic acid encoding the polypeptide in a cultivation medium comprising Quisinostat and trans-2-methyl 2-pentenoic acid, and
 recovering the polypeptide from the cell or the cultivation medium and thereby producing the polypeptide in a eukaryotic cell.

It has been found that a combination of 2M2P and Romidepsin (HDACi) results in increased product yield compared to valproic acid.

Thus, herein is reported a method for the recombinant production of a polypeptide in a eukaryotic cell comprising the steps of:
 cultivating a eukaryotic cell comprising a nucleic acid encoding the polypeptide in a cultivation medium comprising Romidepsin and one of trans-2-methyl 2-pentenoic acid and Flagellin, and
 recovering the polypeptide from the cell or the cultivation medium and thereby producing the polypeptide in a eukaryotic cell.

In one embodiment 2M2P is added to a final concentration in the cultivation medium of about 6-7 mM (about 3 hours after transfection).

In one embodiment Flagellin or Romidepsin are added at a concentration of 2 ng/mL and 15 nM, respectively, 27 h after transfection.

In one embodiment the eukaryotic cell is a mammalian cell. In one embodiment the mammalian cell is a CHO cell or a HEK cell. In one preferred embodiment the mammalian cell is a HEK293 cell.

In one embodiment the expression is a stable or a transient expression. In one preferred embodiment the expression is a transient expression.

In one embodiment the cultivation is for 3 to 16 days. In one embodiment the cultivation is for 3-10 days, preferably if the cell is a HEK cell. In one preferred embodiment the cultivation is for about 7 days.

These findings and aspects are outlined in the following.

Valproic Acid

Figure 1:
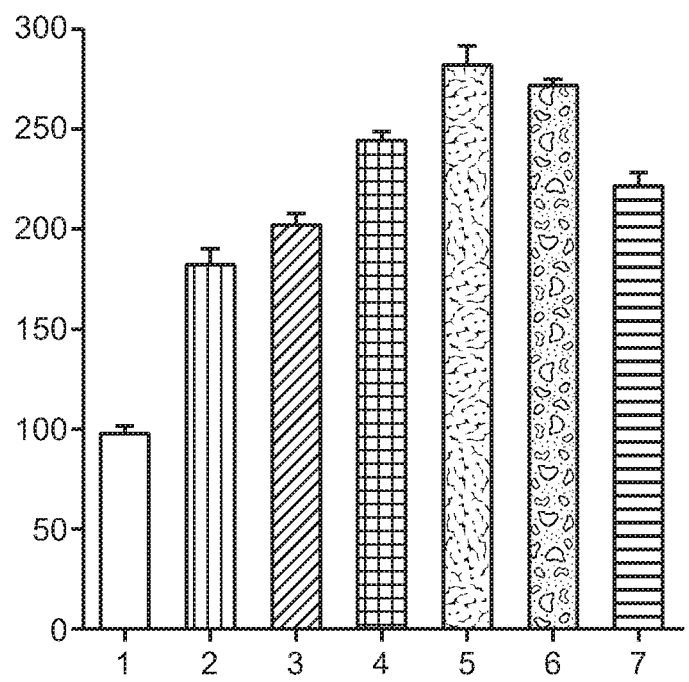
FIG. 1: Relative cell specific productivity of HEK293 cells treated with various VPA concentrations; N=2 for each treatment; y-axis: relative cell specific productivity [%]; 1: control, 2: 0.5 mM valproic acid, 3: 1 mM valproic acid, 4: 2 mM valproic acid, 5: 3 mM valproic acid, 6: 4 mM valproic acid, 7: 6 mM valproic acid.

Different concentrations of valproic acid as sole production enhancer in the range from 0.5 mM to 6 mM were tested (results see following Table and FIG. 1; N=2 for each concentration). The highest specific productivity was observed with 3 mM VPA but with no noteworthy difference in specific productivity to 4 mM VPA. Moreover, the cell specific productivity decreased at higher and lower concentrations.

| compound | relative cell specific productivity [%] |
|---|---|
| none (control) | 100 |
| 0.5 mM valproic acid | 184 |
| 1 mM valproic acid | 204 |
| 2 mM valproic acid | 246 |
| 3 mM valproic acid | 284 |
| 4 mM valproic acid | 273 |
| 6 mM valproic acid | 223 |

Thus, in one embodiment valproic acid is used at a concentration of from 2.5 mM to 5 mM. In one preferred embodiment valproic acid is used at a concentration of from 3 mM to 4 mM. The concentrations given before are independent if valproic acid is used as sole production enhancer in a method as reported herein or in combination with other production enhancers as mixture. Valproic acid as such is used at the recited concentration.

Histone Deacetylase Inhibitors Other than Valproic Acid

Dimethyl sulfoxide (DMSO) was the solvent for all applied HDAC inhibitors to create stock solutions, but at 0.1 vol % DMSO added to a transiently transfected cell culture 3 h after transfection no difference in specific productivity compared to the untreated control was seen (data not shown).

HDAC inhibitors restricted to a certain HDAC subclass as well as broad spectrum HDAC inhibitors were tested towards their effect on cell specific productivity:

Pimelic diphenylamide 106 is a class I HDAC inhibitor with highest affinity towards HDAC 1 and 3, high affinity towards HDAC 2 and modest affinity towards HDAC 8 (Chou, Herman et al. 2008); the inhibitor was added at a concentration range of 0.2-20 µM.

TMP269 is described as an HDAC inhibitor with preference to class IIa HDACs 4, 5, 7, and 9 (Burli, Luckhurst et al. 2013); the inhibitor was added at a concentration range of 0.6-15 µM.

Bufexamac has been described as a selective class IIb HDAC inhibitor (Bantscheff, Hopf et al. 2011); the inhibitor was added at a concentration range of 2-50 µM.

The hydroxamate Belinostat is a broad spectrum inhibitor with highest preference to HDAC 6 and HDAC 1 (Khan, Jeffers et al. 2008; Atadja 2009); the benzamide Entinostat is a class I HDAC inhibitor with additional inhibitory activity to class IIa member HDAC 9 (Bertrand 2010); Mocetinostat is a benzamide with lowest IC50 values for HDAC 1 and 2 and modest inhibitory activity against HDAC 3 and HDAC 11 (Arts, King et al. 2009); Quisinostat is a pyrimidyl hydroxamic acid and a very potent broad spectrum HDAC inhibitor with highest potency towards HDAC 1, 2, 4, and 11 (Arts, King et al. 2009); the broad spectrum HDAC inhibitors Belinostat, Entinostat, Mocetinostat, and Quisinostat were added at the concentrations 1 µM, 300 nM, 2 µM, and 300 nM, respectively.

In contrast to the hypothesis formulated by Backliwal et al. (supra) it has been found by the current inventors that even more potent histone deacetylase inhibitors than valproic acid showed no production enhancing effect (see FIGS. 2A and 2B and the following Table; N=2 (except Bufexamac: N=1)).

| compound | relative cell specific productivity [%] | employed concentration/ dose |
|---|---|---|
| none | 100 | — |
| valproic acid | 326 | 4 mM |
| pimelic diphenylamide 106 | 160 | 20 µM |
| TMP269 | 99 | 15 µM |
| Bufexamac | 94 | 10 µM |
| Belinostat | 115 | 1 µM |
| Entinostat | 108 | 300 nM |
| Mocetinostat | 135 | 2 µM |
| Quisinostat | 279 | 300 nM |

Thus, the effect of valproic acid cannot be obtained by HDACi. In contrast to other HDACi did valproic acid and Quisinostat induce growth inhibition and cell death.

HDAC-Specific Inhibitors

Figure 2A:
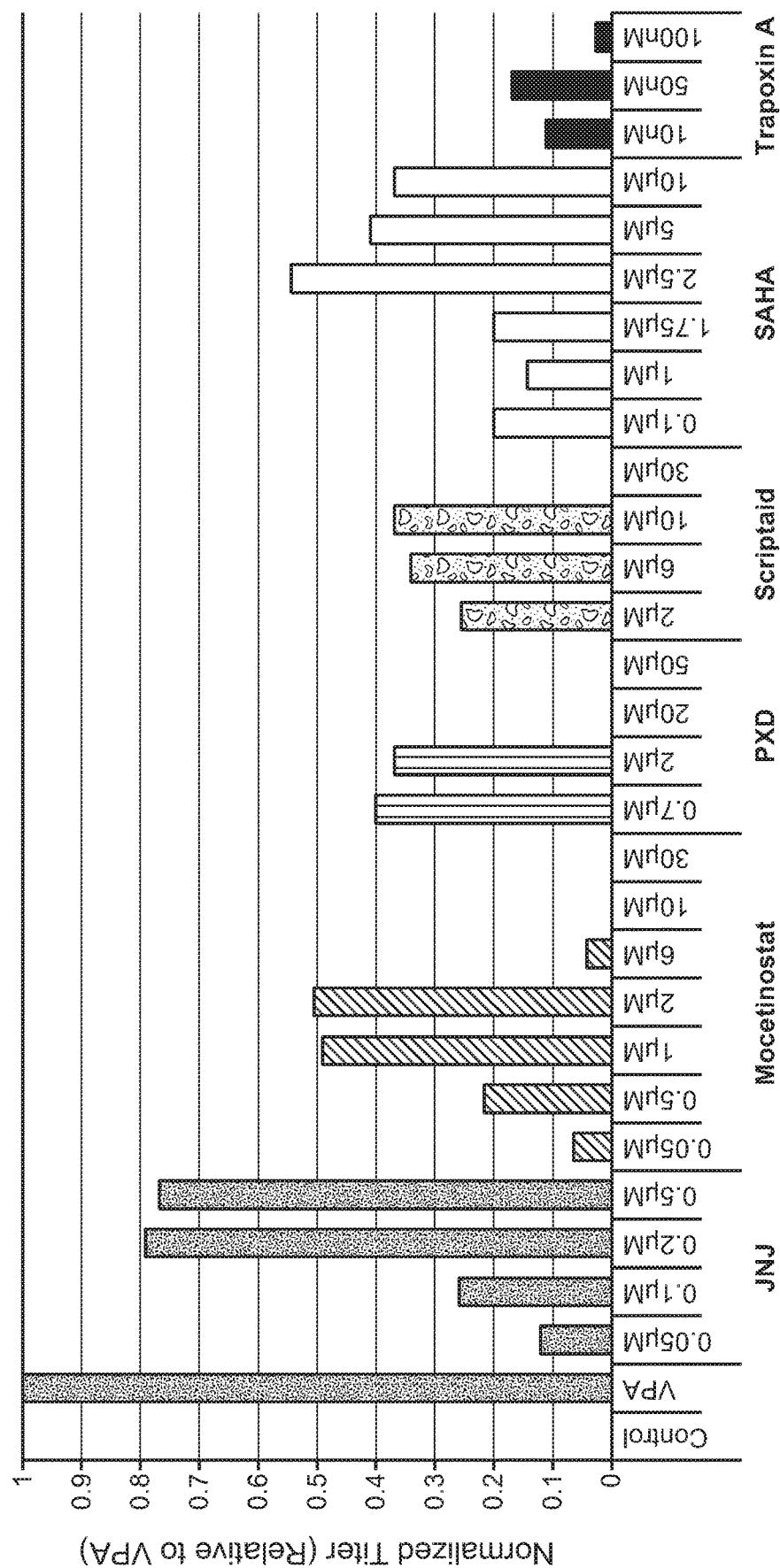
FIGS. 2A and 2B: Effect of different histone deacetylase inhibitors on titer; y-axis: relative cell specific productivity [%]
Figure 2B:
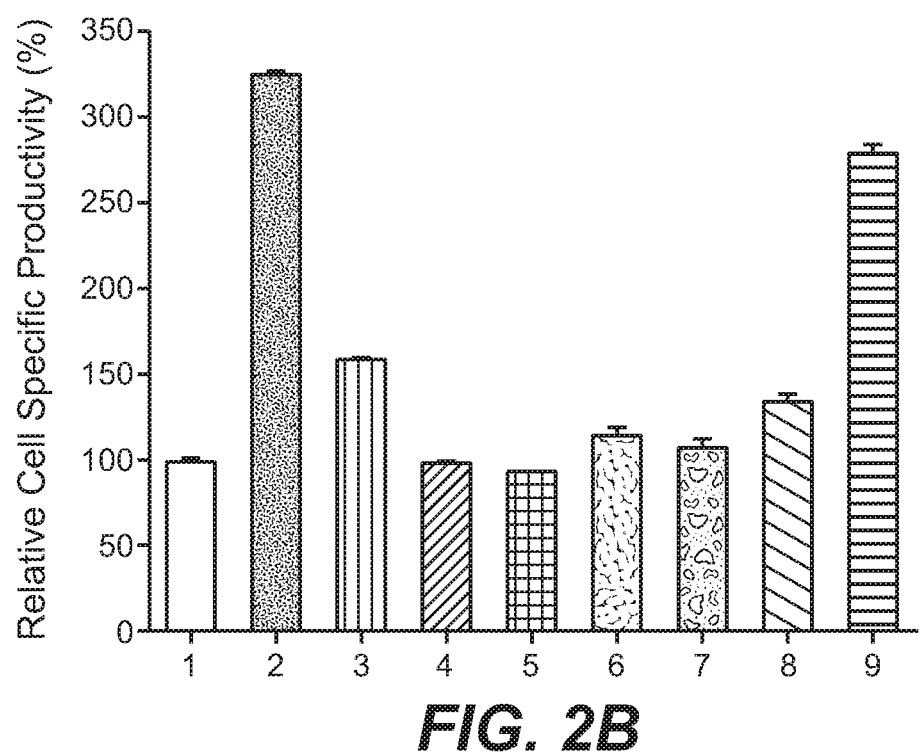

It has been found that the class I HDAC inhibitor pimelic diphenylamide 106 showed an enhancing effect on TGE in contrast to class IIa and class IIb inhibitors (see FIGS. 2A and 2B).

Further different class I isoform-selective HDAC inhibitors have been tested:

The bicyclic depsipeptide Romidepsin is a potent and selective HDAC 1 and HDAC 2 inhibitor (Furumai, Matsuyama et al. 2002); Romidepsin was used with a concentration range from 10 nM to 1 µM.

Apicidin, a cyclic tetrapeptide, is described as a potent class I HDAC inhibitor with highest affinity towards HDAC 2 and HDAC 3 (Khan, Jeffers et al. 2008); the inhibitor was tested at a concentration range from 20 nM to 2 µM.

RGFP966 is a specific HDAC 3 inhibitor; it was used at a concentration range from 1 µM to 100 µM (Malvaez, McQuown et al. 2013).

The HDAC 8-specific inhibitor PCI34051 was added at a concentration ranging from 500 nM to 50 µM (Balasubramanian, Ramos et al. 2008).

The results are shown in the following Tables (see FIG. 7; N=1).

| compound | relative IgG concentration [%] |
|---|---|
| none | 100 |
| 10 nM Romidepsin | 212 |
| 200 nM apicidin | 182 |
| 1 µM RGFP966 | 103 |
| 5 µM PCI34051 | 99 |

| compound | relative titer [%] |
|---|---|
| none | 100 |
| 3 mM valproic acid | 188 |
| 10 nM Romidepsin | 212 |

Valproic Acid Analogs

Several chemical VPA analogues were tested on their effects:

Valpromide (VPM) and trans-2-methyl-2-pentenoic acid (2M2P) are structural VPA analogues which have very weak to no HDAC inhibitory activity (Phiel, Zhang et al. 2001; Gurvich, Tsygankova et al. 2004; Eyal, Yagen et al. 2005).

The HDAC inhibitory activity of Valnoctamide (VCM) is not directly described in the literature, but it is known that the carboxylic acid of VCM, valnoctic acid, has a weak HDAC inhibitory activity (Eyal, Yagen et al. 2005).

HDACi was determined for certain compounds. The results are shown in the following Table and FIGS. 3A and 3B (N=3).

| compound | HDACi [%] | relative cell specific productivity [%] |
|---|---|---|
| control (no inhibition, negative control, not transfected) | 0 | 0 |
| control (negative control, transfected) | — | 100 |
| 10 μM Trichostatin A (positive control) | 99 | — |
| 3 mM valproic acid | 58 | 316 |
| 3 mM valnoctamide | 11.1 | 122 |
| 3 mM 2M2P | 9.4 | 191 |
| 20 μM pimelic diphenylamide 106 | 22.6 | 171 |
| 300 nM Quisinostat | 69 | 339 |

2M2P concentrations from 3 to 11 mM were tested with respect to increase of titer as compared to control (without 2M2P) (N=2).

| 2M2P concentration | relative titer [%] |
|---|---|
| none | 100 |
| 3 mM | 165 |
| 6 mM | 257 |
| 7 mM | 258 |
| 8 mM | 172 |
| 9 mM | 120 |
| 10 mM | 42 |
| 11 mM | 0 (toxic) |

Based on VPA concentrations evaluated above, its analogues were used at a concentration range from 2 mM to 4 mM. At 4 mM, all molecules exhibited high toxicity. VPM was already cytotoxic at 3 mM. Weak TGE enhancement was observed with VPM and VCM at 2 mM. 2M2P clearly increased protein expression yields compared to the negative control at 3 mM (see following Table; FIG. 4; N=2).

| compound | relative cell specific productivity [%] | employed concentration/dose |
|---|---|---|
| none | 100 | — |
| valproic acid | 315 | 4 mM |
| valpromide | 155 | 2 mM |
| valpromide | 0 (toxic) | 3 mM |
| valnoctamide | 133 | 2 mM |
| valnoctamide | 125 | 3 mM |
| 2M2P | 123 | 2 mM |
| 2M2P | 196 | 3 mM |

The results obtained with some compounds are shown in the following Table.

| | — | VPA | VCM | 2M2P |
|---|---|---|---|---|
| chemical structure | — | (structure) | (structure) | (structure) |
| VPA analog | — | — | yes | yes |
| HDAC inhibition | no | yes | no | no |
| HDACi class | — | Aliphatic acid | Aliphatic acid | Aliphatic acid |
| HDAC selectivity | — | Classes I + IIa | — | — |
| Effect on titer/SPR | none | strong | weak | moderate to strong |
| Mean cell specific productivity [pg/cell/24 h] (conc.) | 1.71 | 5.4 (3 mM) | 1.71 (3 mM) | 5.4 (3 mM) |

-continued

| | Quisinostat | PM |
|---|---|---|
| chemical structure | (structure: H3C-indole-CH2-NH-CH2-piperidine-pyrimidine-C(O)-N(H)-OH · HCl) | (structure: H2C-phenyl-NH-C(O)-(CH2)4-C(O)-NH-phenyl-NH2) |
| VPA analog | no | no |
| HDAC inhibition | yes | yes |
| HDACi class | Hydroxamate | Benzamide |
| HDAC selectivity | Classes I + II + IV | Class I |
| Effect on titer/SPR | strong | weak to moderate |
| Mean cell specific productivity [pg/cell/24 h] (conc.) | 1.71 (300 mM) | 5.4 (20 µM) |

NFκB Activators

Is has been found that positive influence on the production yield (titer) can be obtained by modification of NFκB transcription.

It has further been found that the activation of NFκB via canonical and non-canonical pathways leads to production yield increase.

NFκB can be activated via different pathways. The following NFκB activators were tested on their effect:

Tumor necrosis factor (TNF) alpha as well as epidermal growth factor (EGF) and Flagellin from *Salmonella typhimurium* were added at a concentration range of 2 ng/mL-50 ng/mL (Osborn, Kunkel et al. 1989; Sun and Carpenter 1998; Hayashi, Smith et al. 2001).

Betulinic acid and phorbol myristate acetate (PMA) were supplemented in a concentration range between 2.5 µM-40 µM and 10 nM-500 nM, respectively (Kasperczyk, La Ferla-Bruhl et al. 2005; Holden, Squires et al. 2008).

All tested compounds showed an enhancement of cell specific productivity compared to the negative control (see following Table; FIG. 5; N=2).

| compound | relative cell specific productivity [%] |
|---|---|
| none | 100 |
| 50 ng/mL TNFalpha | 139 |
| 50 ng/mL EGF | 173 |
| 10 ng/mL Flagellin | 154 |
| 10 µM betulinic acid | 121 |
| 100 nM PMA | 149 |

Further the inhibition of NFκB was investigated. Since no direct inhibitor of NFκB is available IκB kinases that promote IκB degradation were inhibited by administration of BAY11-7082 (Pierce, Schoenleber et al. 1997).

NFκB can be inhibited by sustained binding of NFκB to its endogenous inhibitor IκB. BAY11-7082 was combined with 3 mM VPA at a concentration range from 5 µM to 15 µM. After high toxicity was observed by combination of VPA with BAY11-7082, several time-points for BAY11-7082 addition were tested. The time point for BAY11-7082 addition with a high effect and the lowest toxicity was 24 h after transfection. The effect of BAY11-7082 lasts for about 4 days. BAY11-7082 was added at the optimal concentration (15 µM) and time point (24 h after transfection) after treatment with VPA, 2M2P or Quisinostat. Cell specific productivity could be significantly reduced with BAY11-7082 addition after VPA and Quisinostat treatment compared to the respective single treatments. No reduction of cell specific productivity was observed with 2M2P in combination with BAY11-7082 as compared to the single treatment. In summary, BAY11-7082 could only reduce the TGE enhancement after treatment with molecules inhibiting HDACs.

Likewise it was examined whether the TGE enhancement by described NFκB activators could be reverted with BAY11-7082. HEK293F cells were treated with TNF, EGF or Flagellin with their respective optimal concentration. Furthermore, BAY11-7082 was added to HEK293F cells treated in the same way 24 hours after stimulation. It can be seen from the data contained in the following Table that TGE enhancement was significantly reduced after BAY11-7082 treatment compared to the corresponding single treatment.

The results are presented in the following Tables (N=3).

| compound | relative cell specific productivity [%] |
|---|---|
| none | 100 |
| 3 mM valproic acid | 237 |
| 3 mM valproic acid + 15 µM BAY 11-7082 | 230 |
| 3 mM 2M2P | 144 |
| 3 mM 2M2P + 15 µM BAY 11-7082 | 149 |
| 300 nM Quisinostat | 218 |
| 300 nM Quisinostat + 15 µM BAY 11-7082 | 205 |
| 50 ng/mL TNFalpha | 157 |
| 50 ng/mL TNFalpha + 15 µM BAY 11-7082 | 115 |
| 20 ng/mL EGF | 151 |
| 20 ng/mL EGF + 15 µM BAY 11-7082 | 133 |
| 2 ng/mL Flagellin | 134 |
| 2 ng/mL Flagellin + 15 µM BAY 11-7082 | 122 |

| compound | specific productivity [pg/cell/day]/after 96 hours |
|---|---|
| none | 2.01 |
| 3 mM valproic acid | 4.92 |
| 1 µM BAY 11-7082 | 2.21 |
| 5 µM BAY 11-7082 | 2.30 |
| 15 µM BAY 11-7082 | 2.27 |
| 1 µM BAY 11-7082 + 3 mM valproic acid | 4.96 |
| 5 µM BAY 11-7082 + 3 mM valproic acid | 4.72 |
| 15 µM BAY 11-7082 + 3 mM valproic acid | 3.84 |
| 3 mM 2M2P | 2.40 |
| 3 mM 2M2P + 15 µM BAY 11-7082 | 2.44 |
| 300 nM Quisinostat | 3.89 |
| 300 nM Quisinostat + 15 µM BAY 11-7082 | 3.64 |
| 50 ng/mL TNFalpha | 2.66 |
| 50 ng/mL TNFalpha + 15 µM BAY 11-7082 | 1.94 |
| 20 ng/mL EGF | 2.56 |
| 20 ng/mL EGF + 15 µM BAY 11-7082 | 2.26 |
| 2 ng/mL Flagellin | 2.27 |
| 2 ng/mL Flagellin + 15 µM BAY 11-7082 | 2.07 |

It can be seen that BAY 11-7082 reduced the production yield increase mediated by HDACi but not by 2M2P. It can further be seen that BAY 11-7082 reduces the production yield increase mediated by NFκB activators.

Combinations i) Without Histone Deacetylase Inhibition

It has been found that the enhancement of TGE by 2M2P cannot be reduced by inhibition of IKK and, thus, that specific productivity was improved by a further mechanism independent from NFκB.

It has been found that 2M2P and NFκB activators can be combined for an increased effect.

Flagellin is a TLR5 agonist. The combination of Flagellin with 2M2P resulted in a production yield increase comparable to that obtained with valproic acid.

In an example HEK293F cells were treated with 2M2P. Additionally, the cells were stimulated with Flagellin 24 h after 2M2P treatment. Flagellin exhibited the mildest toxicity amongst NFκB activators. Cell specific productivity could be further increased by the combination as compared with the individual single treatments. IgG concentration after 2M2P and Flagellin treatment was compared with the yield after VPA treatment. The results are shown in the following Tables and FIGS. 6A and 6B (N=3).

| compound | relative cell specific productivity [%] |
|---|---|
| none | 100 |
| 3 mM 2M2P | 131 |
| 2 ng/mL Flagellin | 135 |
| 3 mM 2M2P + 2 ng/mL Flagellin | 212 |

| compound | relative IgG concentration [%] |
|---|---|
| none | 100 |
| 4 mM valproic acid | 173 |
| 3 mM 2M2P | 128 |
| 2 ng/mL Flagellin | 133 |
| 3 mM 2M2P + 2 ng/mL Flagellin | 175 |

| compound | final titer [mg/L] |
|---|---|
| none | 39.8 |
| 3 mM valproic acid | 68.8 |
| 3 mM 2M2P + 2 ng/mL Flagellin | 69.8 |

This effect is mediated without HDAC inhibition.

ii) With Histone Deacetylase Inhibition

Combination studies of VPA, Quisinostat and 2M2P with each other were performed. To reduce cytotoxicity of VPA, concentration was reduced to 2 mM for combination with the also toxic molecules Quisinostat and 2M2P. The results are shown in the following Tables (N=3).

| compound | relative cell specific productivity [%] |
|---|---|
| none | 100 |
| 2 mM valproic acid | 278 |
| 3 mM 2M2P | 169 |
| 2 mM valproic acid + 3 mM 2M2P | 276 |

| compound | relative IgG concentration [%] |
|---|---|
| none | 100 |
| 2 mM valproic acid | 217 |
| 3 mM 2M2P | 146 |
| 2 mM valproic acid + 3 mM 2M2P | 183 |

| compound | relative cell specific productivity [%] |
|---|---|
| none | 100 |
| 2 mM valproic acid | 278 |
| 300 nM Quisinostat | 258 |
| 2 mM valproic acid + 300 nM Quisinostat | 269 |

| compound | relative IgG concentration [%] |
|---|---|
| none | 100 |
| 2 mM valproic acid | 217 |
| 300 nM Quisinostat | 169 |
| 2 mM valproic acid + 300 nM Quisinostat | 152 |

| compound | relative cell specific productivity [%] |
|---|---|
| none | 100 |
| 3 mM 2M2P | 169 |
| 300 nM Quisinostat | 258 |
| 3 mM 2M2P + 300 nM Quisinostat | 266 |

| compound | relative IgG concentration [%] |
|---|---|
| none | 100 |
| 3 mM 2M2P | 146 |
| 300 nM Quisinostat | 169 |
| 3 mM 2M2P + 300 nM Quisinostat | 152 | iii) Combination of HDAC Inhibitors, NFκB Activators and a VPA Derivative

With the identification of a specific HDAC inhibitor with mild toxicity and strong effect on TGE enhancement, Romidepsin in combination with the NFκB activator Flagellin and the VPA analogue 2M2P create a very effective TGE enhancer combination. Flagellin and Romidep sin were added at a concentration of 2 ng/mL and 15 nM, respectively, 3 hours and 24 h after transfection, respectively. The results are shown in the following Table and in FIGS. 8A and 8B (N=3).

| compound | relative cell specific productivity [%] | relative IgG concentration [%] |
|---|---|---|
| none | 100 | 100 |
| 4 mM valproic acid | — | 173 |
| 2 ng/mL Flagellin | 135 | 128 |
| 15 nM Romidepsin | 203 | 185 |
| 2 ng/mL Flagellin + 15 nM Romidepsin | 213 | 178 |

Romidepsin was also combined with. 2M2P was added at a concentration of 3 mM 3 h after transfection and Romidepsin was added 24 h after 2M2P treatment at a concentration of 15 nM. A synergistic effect was observed in transiently expressed antibody yields. Moreover the combination led to a higher antibody yield compared to the treatment with VPA alone (see the following Table and FIGS. 9A and 9B; N=3).

| compound | relative cell specific productivity [%] | relative IgG concentration [%] |
|---|---|---|
| none | 100 | 100 |
| 4 mM valproic acid | — | 173 |
| 3 mM 2M2P | 131 | 128 |
| 15 nM Romidepsin | 203 | 185 |
| 3 mM 2M2P + 15 nM Romidepsin | 364 | 212 |

Recombinant Methods

Any polypeptide (e.g. an antibody, a single chain antigen binding polypeptide such as a scFv, a scFab, or a darpin, or a multi chain antigen binding polypeptide such as a dsFv or a Fab) can be expressed and purified from the supernatant of eukaryotic cells (e.g. HEK293 cells, CHO cells). It does not matter if the polypeptide is an isolated polypeptide or comprised in a multimeric or heteromeric entity.

Suitable host cells for cloning or expression/secretion of polypeptide-encoding vectors include eukaryotic cells described herein. After expression, the polypeptide may be isolated from the cell or the cultivation supernatant. Thereafter the polypeptide can be further purified.

Vertebrate cells may be used as hosts. For example, mammalian cell lines that are adapted to grow in suspension may be useful. Other examples of useful mammalian host cell lines are the COS-7 cell line (monkey kidney CV1 cell transformed by SV40); the HEK293 cell line (human embryonic kidney); the BHK cell line (baby hamster kidney); the TM4 mouse sertoli cell line (TM4 cells as described, e.g., in Mather, Biol. Reprod. 23 (1980) 243-251); the CV1 cell line (monkey kidney cell); the VERO-76 cell line (African green monkey kidney cell); the HELA cell line (human cervical carcinoma cell); the MDCK cell line (canine kidney cell); the BRL-3A cell line (buffalo rat liver cell); the W138 cell line (human lung cell); the HepG2 cell line (human liver cell); the MMT 060562 cell line (mouse mammary tumor cell); the TRI cell line (e.g. described in Mather, et al., Anal. N.Y. Acad. Sci. 383 (1982) 44-68); the MRCS cell line; and the FS4 cells-line. Other useful mammalian host cell lines include the CHO cell line (Chinese hamster ovary cell), including DHFR negative CHO cell lines (see e.g. Urlaub, et al., Proc. Natl. Acad. Sci. USA 77 (1980) 4216), and myeloma cell lines such as YO, NSO and Sp2/0 cell line. For a review of certain mammalian host cell lines suitable for polypeptide production, see, e.g., Yazaki, and Wu, Methods in Molecular Biology, Antibody Engineering 248 (2004) 255-268 (B. K. C. Lo, (ed.), Humana Press, Totowa, N.J.).

Antibody Fragments

In certain embodiments, the antibody produced with the method as reported herein is an antibody fragment. Antibody fragments include, but are not limited to, Fab, Fab', Fab'-SH, F(ab')2, Fv, and scFv fragments, and other fragments described below. For a review of certain antibody fragments, see Hudson. et al., Nat. Med. 9 (2003) 129-134. For a review of scFv fragments, see, e.g., Plueckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson, et al., Nat. Med. 9 (2003) 129-134; and Holliger, P., et al., Proc. Natl. Acad. Sci. USA 90 (1993) 6444-6448. Triabodies and tetrabodies are also described in Hudson, et al., Nat. Med. 9 (2003) 129-134.

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

Multispecific Antibodies

In certain embodiments, the antibody produced with the method as reported herein is a multispecific antibody, e.g. a bispecific antibody. Multispecific antibodies are monoclonal antibodies that have binding specificities for at least two different sites. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C., and Cuello, Nature 305 (1983) 537-540), WO 93/08829, and Traunecker, A., et al., EMBO J. 10 (1991) 3655-3659), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan, M., et al., Science, 229 (1985) 81-83); using leucine zippers to produce bi-specific antibodies (see, e.g., Kostelny, S. A., et al., J. Immunol., 148(5) (1992) 1547-1553); using "diabody" technology for making bispecific antibody fragments (see, e.g., Hollinger, et al., Proc. Natl. Acad. Sci. USA, 90 (1993) 6444-6448); and using single-chain Fv (sFv) dimers (see, e.g. Gruber, M., et al., J. Immunol., 152 (1994) 5368-5374) and preparing trispecific antibodies as described, e.g., in Tutt, A., et al. J. Immunol. 147 (1991) 60-69.

Engineered antibodies with three or more functional antigen binding sites, including "Octopus antibodies," are also included herein (see, e.g., US 2006/0025576 A1).

The antibody or fragment herein also includes a "Dual Acting Fab" or "DAF" comprising an antigen binding site that binds to CD19 as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

The antibodies as in the current methods can be bispecific antibodies. Bispecific antibodies are a member of the group of multispecific antibodies. Bispecific antibodies comprise at least two binding sites each formed by a pair of an antibody heavy chain variable domain (VH) and an antibody light chain variable domain (VL) binding to different antigens or to different epitopes on the same antigen. Such a bispecific antibody is a 1+1 format. Other bispecific antibody formats are 2+1 formats (comprising two binding sites for a first antigen or epitope and one binding site for a second antigen or epitope) or 2+2 formats (comprising two binding sites for a first antigen or epitope and two binding sites for a second antigen or epitope).

In one embodiment of all aspects the antibody of the current method comprises (all positions according to EU index of Kabat)
  i) a homodimeric Fc-region of the human IgG1 subclass optionally with the mutations P329G, L234A and L235A, or
  ii) a homodimeric Fc-region of the human IgG4 subclass optionally with the mutations P329G, S228P and L235E, or
  iii) a homodimeric Fc-region of the human IgG1 subclass optionally with the mutations P329G, L234A, L235A, I253A, H310A, and H435A, or optionally with the mutations P329G, L234A, L235A, H310A, H433A, and Y436A, or
  iv) a heterodimeric Fc-region whereof
    a) one Fc-region polypeptide comprises the mutation T366W, and the other Fc-region polypeptide comprises the mutations T366S, L368A and Y407V, or
    b) one Fc-region polypeptide comprises the mutations T366W and Y349C, and the other Fc-region polypeptide comprises the mutations T366S, L368A, Y407V, and S354C, or
    c) one Fc-region polypeptide comprises the mutations T366W and S354C, and the other Fc-region polypeptide comprises the mutations T366S, L368A, Y407V and Y349C,
    or
  v) a heterodimeric Fc-region of the human IgG1 subclass whereof both Fc-region polypeptides comprise the mutations P329G, L234A and L235A and
    a) one Fc-region polypeptide comprises the mutation T366W, and the other Fc-region polypeptide comprises the mutations T366S, L368A and Y407V, or
    b) one Fc-region polypeptide comprises the mutations T366W and Y349C, and the other Fc-region polypeptide comprises the mutations T366S, L368A, Y407V, and S354C, or
    c) one Fc-region polypeptide comprises the mutations T366W and S354C, and the other Fc-region polypeptide comprises the mutations T366S, L368A, Y407V and Y349C,
    or
  vi) a heterodimeric Fc-region of the human IgG4 subclass whereof both Fc-region polypeptides comprise the mutations P329G, S228P and L235E and
    a) one Fc-region polypeptide comprises the mutation T366W, and the other Fc-region polypeptide comprises the mutations T366S, L368A and Y407V, or
    b) one Fc-region polypeptide comprises the mutations T366W and Y349C, and the other Fc-region polypeptide comprises the mutations T366S, L368A, Y407V, and S354C, or
    c) one Fc-region polypeptide comprises the mutations T366W and S354C, and the other Fc-region polypeptide comprises the mutations T366S, L368A, Y407V and Y349C,
    or
  vii) a combination of one of i), ii), and iii) with one of vi), v) and vi).

In one embodiment of all aspects the antibody of the current method is a bivalent, bispecific antibody comprising
  a) a first light chain and a first heavy chain of an antibody specifically binding to a first antigen, and
  b) a second light chain and a second heavy chain of an antibody specifically binding to a second antigen, wherein the variable domains VL and VH of the second light chain and the second heavy chain are replaced by each other.

The antibody under a) does not contain a modification as reported under b) and the heavy chain and the light chain under a) are isolated chains.

In the antibody under b)
  within the light chain
    the variable light chain domain VL is replaced by the variable heavy chain domain VH of said antibody, and
  within the heavy chain
    the variable heavy chain domain VH is replaced by the variable light chain domain VL of said antibody.

In one embodiment of all aspects the antibody of the current method is a bivalent, bispecific antibody comprising
  a) a first light chain and a first heavy chain of an antibody specifically binding to a first antigen, and
  b) a second light chain and a second heavy chain of an antibody specifically binding to a second antigen, wherein the variable domains VL and VH of the second light chain and the second heavy chain are replaced by each other, and wherein the constant domains CL and CH1 of the second light chain and the second heavy chain are replaced by each other.

The antibody under a) does not contain a modification as reported under b) and the heavy chain and the light chain and a) are isolated chains.

In the antibody under b)
  within the light chain
    the variable light chain domain VL is replaced by the variable heavy chain domain VH of said antibody, and the constant light chain domain CL is replaced by the constant heavy chain domain CH1 of said antibody;
  and
  within the heavy chain
    the variable heavy chain domain VH is replaced by the variable light chain domain VL of said antibody, and the constant heavy chain domain CH1 is replaced by the constant light chain domain CL of said antibody.

In one embodiment of all aspects the antibody of the current method is a bivalent, bispecific antibody comprising a) a first light chain and a first heavy chain of an antibody specifically binding to a first antigen, and
b) a second light chain and a second heavy chain of an antibody specifically binding to a second antigen, wherein the constant domains CL and CH1 of the second light chain and the second heavy chain are replaced by each other.

The antibody under a) does not contain a modification as reported under b) and the heavy chain and the light chain under a) are isolated chains.

In the antibody under b)
within the light chain
the constant light chain domain CL is replaced by the constant heavy chain domain CH1 of said antibody;
and within the heavy chain
the constant heavy chain domain CH1 is replaced by the constant light chain domain CL of said antibody.

In one embodiment of all aspects the antibody as reported herein is a multispecific antibody, which requires heterodimerization of at least two heavy chain polypeptides.

Heterodimerization

Several approaches for CH3-modifications in order to support heterodimerization have been described, for example in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, and WO 2013/096291. Typically, in the approaches known in the art, the CH3 domain of the first heavy chain and the CH3 domain of the second heavy chain are both engineered in a complementary manner so that the heavy chain comprising one engineered CH3 domain can no longer homodimerize with another heavy chain of the same structure (e.g. a CH3-engineered first heavy chain can no longer homodimerize with another CH3-engineered first heavy chain; and a CH3-engineered second heavy chain can no longer homodimerize with another CH3-engineered second heavy chain). Thereby the heavy chain comprising one engineered CH3 domain is forced to heterodimerize with another heavy chain comprising the CH3 domain, which is engineered in a complementary manner. For this embodiment, the CH3 domain of the first heavy chain and the CH3 domain of the second heavy chain are engineered in a complementary manner by amino acid substitutions, such that the first heavy chain and the second heavy chain are forced to heterodimerize, whereas the first heavy chain and the second heavy chain can no longer homodimerize (e.g. for steric reasons).

The different approaches for supporting heavy chain heterodimerization known in the art, that were cited and included above, are contemplated as different alternatives used in providing a multispecific antibody as reported herein, which comprises a "non-crossed Fab region" derived from a first antibody, which specifically binds to a first antigen, and a "crossed Fab region" derived from a second antibody, which specifically binds to a second antigen, in combination with the particular amino acid substitutions described above.

The CH3 domains of the multispecific antibody as reported herein can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotechnol. 16 (1998) 677-681; Atwell, S., et al., J. Mol. Biol. 270 (1997) 26-35) and increases the yield.

In one preferred embodiment the multispecific antibody comprises a T366W mutation in the CH3 domain of the "knobs chain" and the mutations T366S, L368A, Y407V in the CH3 domain of the "hole-chain" (numbering according to Kabat EU index). An additional interchain disulfide bridge between the CH3 domains can also be used (Merchant, A. M., et al., Nature Biotechnol. 16 (1998) 677-681) e.g. by introducing a Y349C mutation into the CH3 domain of the "knobs chain" and a E356C mutation or a S354C mutation into the CH3 domain of the "hole chain". Thus, in a another preferred embodiment, the multispecific antibody comprises the mutations Y349C and T366W in one of the two CH3 domains and the mutations E356C, T366S, L368A and Y407V in the other of the two CH3 domains or the multispecific antibody comprises the mutations Y349C and T366W in one of the two CH3 domains and the mutations S354C, T366S, L368A and Y407V in the other of the two CH3 domains (the additional Y349C mutation in one CH3 domain and the additional E356C or S354C mutation in the other CH3 domain forming a interchain disulfide bridge) (numbering according to Kabat EU index).

But also other knobs-in-holes technologies as described by EP 1 870 459, can be used alternatively or additionally. In one embodiment the multispecific antibody comprises the mutations R409D and K370E in the CH3 domain of the "knobs chain" and the mutations D399K and E357K in the CH3 domain of the "hole-chain" (numbering according to Kabat EU index).

In one embodiment the multispecific antibody comprises a T366W mutation in the CH3 domain of the "knobs chain" and the mutations T366S, L368A and Y407V in the CH3 domain of the "hole chain" and additionally the mutations R409D and K370E in the CH3 domain of the "knobs chain" and the mutations D399K and E357K in the CH3 domain of the "hole chain" (numbering according to the Kabat EU index).

In one embodiment the multispecific antibody comprises the mutations Y349C and T366W in one of the two CH3 domains and the mutations S354C, T366S, L368A and Y407V in the other of the two CH3 domains, or the multispecific antibody comprises the mutations Y349C and T366W in one of the two CH3 domains and the mutations S354C, T366S, L368A and Y407V in the other of the two CH3 domains and additionally the mutations R409D and K370E in the CH3 domain of the "knobs chain" and the mutations D399K and E357K in the CH3 domain of the "hole chain" (numbering according to the Kabat EU index).

Apart from the "knob-into-hole technology" other techniques for modifying the CH3 domains of the heavy chains of a multispecific antibody to enforce heterodimerization are known in the art. These technologies, especially the ones described in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291 are contemplated herein as alternatives to the "knob-into-hole technology" in combination with a multispecific antibody.

In one embodiment of all aspects and embodiments as reported herein the multispecific antibody is a bispecific antibody or a trispecific antibody. In one preferred embodiment the multispecific antibody is a bispecific antibody.

In one embodiment of all aspects as reported herein, the antibody is a bivalent or trivalent antibody. In one embodiment the antibody is a bivalent antibody.

In one embodiment of all aspects as reported herein, the multispecific antibody has a constant domain structure of an IgG type antibody. In one further embodiment of all aspects as reported herein, the multispecific antibody is of human subclass IgG1, or of human subclass IgG1 with the mutations L234A and L235A. In one further embodiment of all aspects as reported herein, the multispecific antibody is of human subclass IgG2. In one further embodiment of all aspects as reported herein, the multispecific antibody is of human subclass IgG3. In one further embodiment of all aspects as reported herein, the multispecific antibody is of human subclass IgG4, or of human subclass IgG4 with the additional mutation S228P. In one further embodiment of all aspects as reported herein, the multispecific antibody is of human subclass IgG1, or of human subclass IgG4. In one further embodiment of all aspects as reported herein, the multispecific antibody is of human subclass IgG1 with the mutations L234A and L235A (numbering according to Kabat EU index). In one further embodiment of all aspects as reported herein, the multispecific antibody is of human subclass IgG1 with the mutations L234A, L235A and P329G (numbering according to Kabat EU index). In one further embodiment of all aspects as reported herein, the multispecific antibody is of human subclass IgG4 with the mutations S228P and L235E (numbering according to Kabat EU index). In one further embodiment of all aspects as reported herein, the multispecific antibody is of human subclass IgG4 with the mutations S228P, L235E and P329G (numbering according to Kabat EU index).

The antibody in the methods as reported herein is in one embodiment of human subclass IgG1 with mutations PVA236, L234A/L235A, and/or GLPSS331 (numbering according to EU index of Kabat), or of subclass IgG4. In a further embodiment, the antibody is of any IgG class, in one embodiment of the subclass IgG1 or IgG4, containing at least one mutation in E233, L234, L235, G236, D270, N297, E318, K320, K322, A327, A330, P331 and/or P329 (numbering according to EU index of Kabat). It is further in one embodiment that the antibody is of the IgG4 subclass and contains the mutation S228P, or the mutations S228P and L235E (Angal, S., et al., Mol. Immunol. 30 (1993) 105-108) (numbering according to EU index of Kabat).

The C-terminus of the heavy chain of the antibody in the methods as reported herein can be a complete C-terminus ending with the amino acid residues PGK. The C-terminus of the heavy chain can be a shortened C-terminus in which one or two of the C-terminal amino acid residues have been removed. In one preferred embodiment the C-terminus of the heavy chain is a shortened C-terminus ending PG.

In one embodiment the antibody comprises a heavy chain including a C-terminal CH3 domain as specified herein, comprises the C-terminal glycine-lysine dipeptide (G446 and K447, numbering according to Kabat EU index). In one embodiment the antibody comprises a heavy chain including a C-terminal CH3 domain, as specified herein, comprises a C-terminal glycine residue (G446, numbering according to Kabat EU index).

Examples

The following examples, figures and sequences are provided to aid the understanding of the present invention, the true scope of which is set forth in the appended claims. It is understood that modifications can be made in the procedures set forth without departing from the spirit of the invention.

Materials and Methods

Used Chemicals

| Name | Manufacturer |
| --- | --- |
| 2-Methyl-2-pentenoic acid | Sigma Aldrich |
| Acetic acid | Sigma Aldrich |
| Apicidin | Sigma Aldrich |
| BAY11-7082 | Sigma Aldrich |
| Belinostat | Selleckchem |
| Beta-Mercaptoethanol | Sigma Aldrich |
| Bovine Serum Albumin | Sigma Aldrich |
| Dimethyl sulfoxide | Sigma Aldrich |
| Entinostat | Selleckchem |
| Epidermal Growth Factor | Sigma Aldrich |
| Ethanol | Sigma Aldrich |
| Flagellin | Sigma Aldrich |
| Glucose | Sigma Aldrich |
| PCI34051 | Selleckchem |
| JetPEI | Polyplus |
| Mocetinostat | Selleckchem |
| Pimelic Diphenylamide | Cayman Chemicals |
| Quisinostat | Selleckchem |
| RGFP966 | Selleckchem |
| RNAse free Water | Life Technologies |
| Romidepsin | Selleckchem |
| TMP269 | Xcessbio Biosciences |
| Tumor Necrosis Factor | Sigma Aldrich |
| Valnoctamide | Sigma Aldrich |
| Valproic acid | Sigma Aldrich |
| Valpromide | Sigma Aldrich |

Kits and Mastermixes

| Name | Manufacturer |
| --- | --- |
| Transcriptor first strand cDNA synthetase | Roche |
| Taq Man probes Master | Roche |
| HDAC activity assay | Biovision |
| RNeasy plus Mini kit | Qiagen |
| Agilent RNA 6000 Nano Kit | Agilent |

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis. The synthesized gene fragments were cloned into an E. coli plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Description of the Basic/Standard Mammalian Expression Plasmid

For the expression of a desired gene/protein (e.g. full length antibody heavy chain, full length antibody light chain, or an Fc-chain containing an oligoglycine at its N-terminus) a transcription unit comprising the following functional elements is used:

the immediate early enhancer and promoter from the human cytomegalovirus (P-CMV) including intron A, a human heavy chain immunoglobulin 5'-untranslated region (5' UTR), a murine immunoglobulin heavy chain signal sequence, a gene/protein to be expressed (e.g. full length antibody heavy chain), and the bovine growth hormone polyadenylation sequence (BGH pA).

Beside the expression unit/cassette including the desired gene to be expressed the basic/standard mammalian expression plasmid contains an origin of replication from the vector pUC18 which allows replication of this plasmid in *E. coli*, and a beta-lactamase gene which confers ampicillin resistance in *E. coli*.

Cell Cultivation

HEK293F cells were cultivated in F17 medium (Life Technologies) in shaker flasks at 36.5° C., 7.0% $CO_2$ and 80% humidity in a shaker incubator (Kuhner, Mytron). Cells were split every three to four days and were cultivated no longer than five weeks. To avoid overgrowth and to keep them in the exponential phase of growth, viable cell densities (VCD) never exceeded $60*10^5$ cells/mL.

Transient Gene Expression (TGE)

Transient gene expression is a 5-7 days lasting procedure. The standard operating procedure of this expression system is applicable to shaker flasks with various volumes of cell culture ranging from 80 mL to 2 L. First, half of the cell culture volume is seeded at a viable cell density (VCD) of $8*10^5$ cells/mL. After two days of cultivation, cells are split to a VCD of about $12*10^5$ cells/mL. On the next day, cells are transfected with a polyethylene imine (PEI)-based transfection reagent at a VCD between $20*10^5$ cells/mL and $25*10^5$ cells/mL. 3 hours after transfection, the production enhancer (if any) is added. 24 h after transfection, a feeding solution and a glucose bolus is supplemented to avoid the limitation of nutrients. Depending on cell viability, which should not decrease below 50%, the supernatant is harvested five to seven days post transfection and subjected to antibody purification.

To compare transient gene expression rates always the same plasmids encoding for one distinct antibody were co-transfected.

To co-transfect two plasmids equimolarily, the ratio of the base pair number of one plasmid to the total base pair number was calculated and multiplied with the total amount of DNA (0.5 mg/L). Plasmid one has a size of 10530 bp and plasmid two has a size of 7184 bp and were solved in water to a final concentration of 1 mg/mL. For transfection of one liter cell culture, 297 µL of plasmid one and 203 µl of plasmid two were dissolved in 40 mL phosphate buffered saline (PBS) at room temperature. 1.25 mL JetPEI® solution was added and the solution was mixed well. After incubation for 10-15 min., the mixture was added to the cells. The cells were transfected in a batch containing the whole cell culture necessary for every experiment to avoid variance arising from different transfection efficiencies.

80 mL of the transfected cell culture batch was added to a 125 ml shaker flask. For every experiment, two or three 125 mL shaker flasks were used as biological replicates and treated the same way. Three hours after transfection, cells were split into 125 mL shaker flasks and the cellular treatments with small molecules or ligands were started. Basal protein expression was determined by untreated control samples. To compare samples with the standard operating procedure, cells were also treated with VPA to a final concentration of 4 mM or 3 mM. VPA and its analogues were dissolved in double distilled water. HDAC inhibitors and BAY 11-7082 were dissolved in dimethyl sulfoxide (DMSO) and stock solutions were prepared with a 1000-fold higher concentration as the final concentration. Epidermal growth factor (EGF) was reconstituted in 10 mM sterile acetic acid supplemented with 0.1% bovine serum albumin (BSA). Tumor necrosis factor (TNF) alpha was reconstituted with PBS supplemented with 0.1% BSA. Flagellin was dissolved in sterile double distilled water. The applied molecules were not added to the cultivation directly, but diluted in 16 mL medium pre-warmed to 36.5° C. and added to the cultivation thereafter.

24 h after transfection a feeding solution at 36.5° C. and 3 mg/mL glucose were added to the cultivation.

Determination of Cell Density and Viability

To determine cell viability and viable cell density (VCD) 1 mL cultivation medium (cell suspension) was transferred into a Cedex low fouling sample cup. The cup was placed into a Vicell instrument (Beckman Coulter). The instrument mixes cells with trypan blue to stain dead cells. After analysis of 50 images VCD was calculated and viability was determined by calculation of the percentage of viable cell number in relation to the total cell number.

Determination of IgG concentration

Total concentration of the transiently expressed antibody was determined by a turbidimetric test. One mL cell suspension was transferred into an Eppendorf cup and centrifuged for 10 min. at 10,000 rpm (9,300 g). The supernatant was transferred into a new cup and subjected to Cobas Integra 400 plus (Roche) analysis. With comparison to internal standard the absolute concentration was calculated.

Cell Specific Productivity

Cell specific productivity is the protein production per cell and per day. The calculation is based on the formula to calculate the change of product concentration (ΔP) per elapsed time (Δt):

$$\frac{\Delta P}{\Delta t} = p_r * c(t).$$

$p_r$ = specific productivity rate; $c(t)$ = productive biomass

For the reason that the productivity refers to one cell, the productive biomass is the mean viable cell density ($\overline{VCD}$). Transformed to calculate the cell specific productivity, the formula ends in:

$$p_r = \frac{\Delta P}{(VCD_{t1} + VCD_{t2}) * 0.5 * \Delta t}$$

To transform the unit into [pg/(cell*d)] the formula was adapted as follows:

$$p_r\left(\frac{pg}{cell*d}\right) = \frac{\left(P_2\left(\frac{mg}{L}\right) - P_1\left(\frac{mg}{L}\right)\right)}{\left(VCD_{t1}(*10^5 \frac{cells}{mL}) + VCD_{t2}(*10^5 \frac{cells}{mL})\right)*10*0.5*(t_2(d)-t_1(d))}$$

Afterwards, the mean specific productivity over the whole cultivation time was calculated. Finally the value of the mean specific productivities relative to the transfected negative control was determined.

HDAC Activity Determination

HDAC activity was determined by the in situ HDAC activity fluorimetric assay kit (Biovision) according to the manufacturer's instructions. HEK293F cells were suspended in F17 medium (Life Technologies) to a cell density of $5*10^5$ cells/mL. One hundred micro liter culture was pipetted per well into a black ELISA plate. The plate was centrifuged at 1000 g for 5 min. The supernatant was discarded and the cells were resuspended in a reaction mix containing F17 medium, 1% HDAC substrate and the molecule tested towards HDAC inhibitory activity. 10 µM Trichostatin A was used as a positive control and the basal HDAC activity was determined by re-suspending the cells in F17 medium with 1% HDAC substrate. Furthermore, cells were resuspended in F17 medium without HDAC substrate as a background control. The HDAC activity assay was performed in triplicates for every sample as well as every control. The 96-well plate was incubated at 36.5° C., 80% humidity and 7% $CO_2$ for one hour. During this time, the active HDACs deacetylate the HDAC substrate what releases the quenched fluorescent signal of the substrate. After incubation the fluorescent signal was analyzed by the infinite fluorescence plate reader (TECAN). The fluorescence signal of the samples and controls was normalized by subtracting the fluorescence signal of the background control. It is assumed that the fluorescent signal arising from deacetylation of the substrate directly correlates with HDAC activity. The HDAC inhibition was calculated relative to the positive control (100% inhibition) and the negative control (0% inhibition).

Flow Cytometry

To determine transfection efficiencies after transfection of fluorescent RNA, cells were analyzed by flow cytometry using FACS Canto II (BD). Cell suspension (2 mL) was transferred into a 2 mL Eppendorf cup and centrifuged 10 min. at 1,500 rpm (200 g). To reduce background fluorescence the supernatant was discarded and cells were resuspended in 2 mL F17 medium. The cell suspension was transferred into a 14 mL round bottom polystyrene tube (Falcon) and kept in the dark. Ten thousand cells were analyzed at 488 nm excitation and 525 nm emission wavelengths. The viable population was further analyzed using the FlowJo software. The signal strength was compared to a non-transfected control sample and transfection efficiency was determined.

Fluorescence Microscopy

Nuclei of FITC-labeled RNA transfected cells were counterstained by adding two drops of a Hoechst33343 solution (Life Technologies) per mL cell suspension and incubation for 20 min. Cells were imaged by a fluorescence microscope (Zeiss) to determine transfection efficiencies qualitatively.

Statistics of Cell and Molecular Biological Experiments

Cell specific productivities, relative enhancement, as well as relative IgG concentration were initially analyzed by one-way ANOVA for significance. Treatments were compared by a Student's t-test to determine the level of significance (p-value). The level of significance is displayed as asterisk. One asterisk corresponds to a p-value ≤0.05, two asterisks correspond to a p-value ≤0.01, three asterisks to a p-value ≤0.001.

LITERATURE

Alberts, B. and J. H. Wilson, et al. (2008). Molecular biology of the cell. New York, Garland Science.
Arts, J., et al., Clin. Cancer Res 15 (2009) 6841-6851.
Ashburner, B. P., et al., Mol. Cell. Biol. 21 (2001) 7065-7077.
Atadja, P., Cancer Lett. 280 (2009) 233-241.
Backliwal, G., et al., Biotechnol. Bioeng. 101 (2008) 182-189.
Baeuerle, P. A. and D. Baltimore, Science 242 (1988*) 540-546.
Balasubramanian, S., et al., Leukemia 22 (2008) 1026-1034.
Baldwin, A. S., Jr., Ann. Rev. Immunol. 14 (1996) 649-683.
Bantscheff, M., et al., Nat. Biotechnol. 29 (2011) 255-265.
Bertrand, P., Eur. J. Med. Chem. 45 (2010) 2095-2116.
Biswas, D. K., et al., Proc. Natl. Acad. Sci. USA 97 (2000) 8542-8547.
Bjerkedal, T., et al., Lancet 2 (1982) 1096.
Blaheta, R. A. and J. Cinatl, Jr., Med. Res. Rev. 22 (2002) 492-511.
Blaheta, R. A., et al., Med. Res. Rev. 25 (2005) 383-397.
Bode, A. M. and Z. Dong, Nat. Rev. Cancer 4 (2004) 793-805.
Bolden, J. E., et al., Nat. Rev. Drug Discov. 5 (2006) 769-784.
Bolton, E., et al., Ann. Rep. Comput. Chem. Volume 4 (2008).
Burli, R. W., et al., J. Med. Chem. 56 (2013) 9934-9954.
Caillaud, A., et al., J. Biol. Chem. 277 (2002) 49417-49421.
Chateauvieux, S., et al., J. Biomed. Biotechnol. 2010.
Chen, F. E., et al., Prot. Eng. 12 (1999) 423-428.
Chen, G., et al., J. Neurochem. 72 (1999) 1327-1330.
Chen, G., et al., Neurochem. 63 (1994) 2361-2364.
Chen, G., et al., Bipolar disorders 2 (3 Pt 2, 2000) 217-236.
Chen, L., et al., Science 293 (2001) 1653-1657.
Chen, L. F., et al., EMBO J. 21 (2002) 6539-6548.
Chen, Z. J., et al., Cell 84 (1996) 853-862.
Chou, C. J., et al., J. Biol. Chem. 283 (2008) 35402-35409.
Chung, S. Y., et al., Proc. Natl. Acad. Sci. USA 75 (1978) 1680-1684.
Clapier, C. R. and B. R. Cairns, Ann. Rev. Biochem. 78 (2009) 273-304.
Dai, Y., et al., Mol. Cell. Biol. 25 (2005) 5429-5444.
DiDonato, J. A., et al., Nature 388 (1997) 548-554.
Eickholt, B. J., et al., Mol. Pharm. 67 (2005) 1426-1433.
Eikel, D., et al., Chem. Res. Toxicol. 19 (2006) 272-278.
Eyal, S., et al., Biochem. Pharmacol. 69 (2005) 1501-1508.
Fischle, W., Methods 36 (2005): 362-367.
Fontes, M. and C. Soneson (2011), BMC bioinformaticals 12 (2011) 307.
Fujiki, R., et al., Cell Death Dis. 20 (2013) 4:e677.
Furumai, R., et al., Cancer Res. 62 (2002) 4916-4921.
Ghosh, S. (2007). Handbook of transcription factor NF-kappaB. Boca Raton, CRC Press.
Giavini, E. and E. Menegola, Curr. Pharm. Design. 20 (2014) 5438-5442.
Gloire, G., et al., Biochem. Pharmacol. 72 (2006) 1493-1505.
Gottlicher, M., et al., EMBO J. 20 (2001) 6969-6978.
Grimm, S. and P. A. Baeuerle, Biochem. J. 290 (1993) 297-308.
Gurvich, N., et al., Cancer Res. 64 (2004) 1079-1086.
Hacker, D. L., et al., Prot. Expr. Purif. 92 (2013) 67-76.
Han, B. R., et al., Onc. Reports 30 (2013) 2999-3005.
Hayashi, F., et al., Nature 410 (2001) 1099-1103.
Hebbar, P. B. and T. K. Archer, J. Biol. Chem. 283 (2008) 4595-4601.
Heusch, M., et al., Oncogene 18 (1999) 6201-6208.
Holden, N. S., et al., Cell. Sig. 20 (2008) 1338-1348.
Jenuwein, T. and C. D. Allis, Science 293 (2001) 1074-1080.
Jiang, C. and B. F. Pugh, Nat. Rev. Gen. 10 (2009) 161-172.

Kasperczyk, H., et al., Oncogene 24 (2005) 6945-6956.
Khan, N., et al., Biochem. J. 409 (2008) 581-589.
Khobta, A., et al., Nuc. Acids Res. 38 (2010) 4285-4295.
Kramer, A., et al., Bioinformat. 30 (2014) 523-530.
Kuriyan, J. and D. Thanos, Structure 3 (1995) 135-141.
Lallena, M. J., et al., Mol. Cell. Biol. 19 (1999) 2180-2188.
Leszczyniecka, M., et al., Pharmacol. Therapeut. 90 (2001) 105-156.
Li, B., et al., Cell 128 (2007) 707-719.
Lin, L. and S. Ghosh, Mol. Cell. Biol. 16 (1996) 2248-2254.
Ludtmann, M. H., et al., Seminars in cell & developmental biology 22 (2011) 105-113.
Luger, K., et al., Nature 389 (1997) 251-260.
Malvaez, M., et al., Proc. Natl. Acad. Sci. USA 110 (2013) 2647-2652.
Martin, M. L. and C. M. Regan, Brain Res. 554 (1991) 223-228.
May, M. J. and S. Ghosh, Seminars in cancer biology 8 (1997) 63-73.
Minucci, S. and P. G. Pelicci, Nat. Rev. Cancer 6 (2006) 38-51.
Osborn, L., et al., Proc. Natl. Acad. Sci. USA 86 (1989) 2336-2340.
Phiel, C. J., et al., J. Biol. Chem. 276 (2001) 36734-36741.
Pierce, J. W., et al., J. Biol. Chem. 272 (1997) 21096-21103.
Riu, E., et al., Mol. Therap. 15 (2007) 1348-1355.
Ropero, S. and M. Esteller, Mol. Oncol. 1 (2007) 19-25.
Sen, R. and D. Baltimore, Cell 47 (1986) 921-928.
Slesinger, P. A. and H. S. Singer, Epilepsia 28 (1987) 214-221.
Struhl, K., Cell 98 (1999) 1-4.
Sun, L. and G. Carpenter, Oncogene 16 (1998) 2095-2102.
Suzuki, M., et al., J. Virol. 80 (2006) 3293-3300.
Totzke, G., et al., J. Biol. Chem. 281 (2006) 12645-12654.
Verstrepen, L., et al., Cell. Mol. Life Sci. 65 (2008) 2964-2978.
Werling, U., et al., Mol. Pharmacol. 59 (2001) 1269-1276.
Woodcock, C. L., et al., Exp. Cell Res. 97 (1976) 101-110.
Xu, W. S., et al., Oncogene 26 (2007) 5541-5552.
Yamaoka, S., et al., Cell 93 (1998) 1231-1240.
Yuan, P. X., et al., J. Biol. Chem. 276 (2001) 31674-31683.
Yuan, Z. L., et al., Science 307 (2005) 269-273.
Zilberman, Y., et al., J. Cell Sci. 122 (2009) 3531-3541.

The invention claimed is:

1. A method for the recombinant production of a polypeptide in a eukaryotic cell comprising the steps of:
cultivating a eukaryotic cell comprising a nucleic acid encoding the polypeptide in a cultivation medium comprising a compound selected from the group consisting of trans-2-methyl 2-pentenoic acid, the broad-spectrum HDAC inhibitor Quisinostat, and the subtype-specific HDAC inhibitor Romidepsin, and
recovering the polypeptide from the cell or the cultivation medium and thereby producing the polypeptide in a eukaryotic cell.

2. A method for the recombinant production of a polypeptide in a eukaryotic cell comprising the steps of:
cultivating a eukaryotic cell comprising a nucleic acid encoding the polypeptide in a cultivation medium comprising a first and a second compound selected from the group of compounds consisting of trans-2-methyl 2-pentenoic acid, subtype-specific HDAC inhibitors, and canonical and non-canonical NFκB activators, and
recovering the polypeptide from the cell or the cultivation medium and thereby producing the polypeptide in a eukaryotic cell.

3. The method according to claim 2, wherein the canonical NFκB activator is selected from the group consisting of TNFalpha, ligands of IL-1R/TLR, lipopolysaccharides and IL-1b.

4. The method according to claim 2, wherein the non-canonical NFκB activator is selected from the group consisting of EGF, PMA, and betulinic acid.

5. The method according claim 2, wherein the subtype-specific HDAC inhibitor is an HDAC-1 and/or HDAC-2 and/or HDAC-3 inhibitor.

6. The method according to claim 5, wherein the subtype-specific HDAC inhibitor is selected from the group consisting of pimelic diphenylamide 106, Apicidin, and Romidepsin.

7. The method according to claim 2, wherein the first compound is trans-2-methyl 2-pentenoic acid and the second compound is Flagellin.

8. The method according to claim 2, wherein the first compound is trans-2-methyl 2-pentenoic acid and the second compound is Quisinostat.

9. The method according claim 2, wherein the first compound is Romidepsin and the second compound is trans-2-methyl 2-pentenoic acid or Flagellin.

10. The method according to claim 1, wherein the compound is added from one hour to five hours after transfection of the cells.

11. The method according to claim 10, wherein the compound is added about three hours after the transfection of the cells to the cultivation.

12. The method according to claim 2, wherein the second compound is added from one hour to five hours after transfection of the cells.

13. The method according to claim 12, wherein the second compound is added about twenty-four to twenty-seven hours after the transfection of the cells to the cultivation.

14. The method according to claim 1, wherein the trans-2-methyl 2-pentenoic acid is added to a final concentration in the cultivation medium of about 6-7 mM.

15. The method according claim 9, wherein the Flagellin is added to a final a concentration of 2 ng/mL and the Romidepsin is added to a final concentration of 15 nM.

16. The method according to claim 9, wherein the polypeptide is an antibody.

17. The method according to claim 1, wherein the eukaryotic cell is a CHO cell or a HEK cell.

18. The method according to claim 2, wherein the first compound is added from one hour to five hours after transfection of the cells.

19. The method according to claim 18, wherein the first compound is added about three hours after the transfection of the cells to the cultivation.

20. The method according to claim 2, wherein trans-2-methyl 2-pentenoic acid is added to a final concentration in the cultivation medium of about 6-7 mM.

21. The method according to claim 2, wherein the polypeptide is an antibody.

22. The method according to claim 2, wherein the eukaryotic cell is a CHO cell or a HEK cell.

* * * * *